United States Patent [19]
Erlich et al.

[11] Patent Number: 6,040,166
[45] Date of Patent: Mar. 21, 2000

[54] KITS FOR AMPLIFYING AND DETECTING NUCLEIC ACID SEQUENCES, INCLUDING A PROBE

[75] Inventors: Henry A. Erlich, Oakland; Glenn Horn, Emeryville; Randall K. Saiki, Richmond; Kary B. Mullis, La Jolla; David H. Gelfand, Oakland, all of Calif.

[73] Assignee: Roche Molecular Systems, Inc., Pleasanton, Calif.

[21] Appl. No.: 08/312,729

[22] Filed: Sep. 27, 1994

Related U.S. Application Data

[62] Division of application No. 07/546,257, Jun. 28, 1990, abandoned, which is a division of application No. 07/063,647, Jun. 17, 1987, Pat. No. 4,965,188, which is a continuation-in-part of application No. 06/899,513, Aug. 22, 1986, abandoned, which is a continuation-in-part of application No. 06/839,331, Mar. 13, 1986, abandoned, and a continuation-in-part of application No. 06/828,144, Feb. 7, 1986, Pat. No. 4,683,195, which is a continuation-in-part of application No. 06/824,044, Jan. 30, 1986, abandoned, which is a division of application No. 06/791,308, Oct. 25, 1985, Pat. No. 4,683,202, which is a continuation-in-part of application No. 06/716,975, Mar. 28, 1985, abandoned.

[51] Int. Cl.⁷ ..................................................... C12N 9/12
[52] U.S. Cl. .............................. 435/194; 435/6; 435/91.2; 536/23.1
[58] Field of Search ............................ 435/6, 69.1, 91.2, 435/172.3, 194, 320.1; 536/23.1, 24.3–24.33; 935/17.6, 76–78; 436/63, 94, 501, 508

[56] References Cited

U.S. PATENT DOCUMENTS

| | | | |
|---|---|---|---|
| 4,358,535 | 11/1982 | Falkow et al. | 435/5 |
| 4,486,539 | 12/1984 | Ranki et al. | 436/504 |
| 4,683,195 | 7/1987 | Mullis et al. | 435/6 |
| 4,683,202 | 7/1987 | Mullis | 435/91.2 |
| 4,851,331 | 7/1989 | Vary et al. | 435/6 |
| 4,889,818 | 12/1989 | Gelfand et al. | 435/194 |

FOREIGN PATENT DOCUMENTS

| | | |
|---|---|---|
| 090 433 A1 | 10/1983 | European Pat. Off. . |
| 0135108 | 3/1985 | European Pat. Off. . |
| 138 242 A1 | 4/1985 | European Pat. Off. . |
| 2019408 | 10/1979 | United Kingdom . |
| 8402721 | 7/1984 | WIPO . |

OTHER PUBLICATIONS

Kleppe et al., 1971, "Studies on Polynucleotides—Repair Replication of Short Synthetic DNA's as Catalyzed by DNA Polymerases" J. Mol. Biol. 56:341–361.
Besmer et al., 1972, "Studies on Polynucleotides—Hybridization of Polydeoxynucleotides with Tyrosine Transfer RNA Sequences to the r–Strand of phi–80 psu+III DNA" J. Mol. Biol. 72:502–522.
Khorana et al., 1972, "Studies on Polynucleotides—Total Synthesis of the Structural Gene for an Alanine Transfer Ribonucleic Acid from Yeast" J. Mol. Biol. 72:209–217.
Panet and Khorana, 1974, "The Linkage of Deoxyribopolynucleotide Templates to Cellulose and its Use in Their Replication" J. Biological Chemistry 249(16):5213–5221.
Olson et al., Jan., 1975, "Enzymatic Multiplication of a Chemically Synthesized DNA Fragment" Nucleic Acids Research 2(1):43–60.
Research Awards Index, Fiscal Year 1976, p. 2565, Publication No. (NIH) 77–200.
Research Awards Index, Fiscal Year 1977, p. 2812, Publication No. (NIH) 78–200.
Research Awards Index, Fiscal Yeae 1978, page number unavailable, Publication No. (NIH) 79–200.
Salser, in *Genetic Engineering*, "Cloning cDNA Sequences: A General Technique for Propagating Eurakyotic Gene Sequences in Bacterial Cells" 1978, Chakrabarty (ed.), CRC Press Inc., Boca Raton Florida, pp. 53–81.
Research Awards Index, Fiscal Year 1979, p. 1742, Publication No. (NIH) is unavailable.
Houghton et al., 1980, "The Complete Amino Acid Sequence of Human Fibroblast Interferon as Deduced Using Synthetic Oligodeoxyribonucleotide Primers of Reverse Transcriptase" Nucleic Acids Research 8(13):2885–2894.
Research Awards Index, Fiscal Year 1980, pp. 1312 and 1802, Publication No. (NIH) 81–200.
Hong, 1981, "A Method for Sequencing Single–Stranded Cloned DNA in Both Directions" Bioscience Reports 1:243–252.
Kaboev et al., Jan., 1981, "Purification and Properties of Deoxyribonucleotide Acids Polymerase from *Bacillus Stearothermophilus*" J. Bacteriology 145(1):21–26.
Kaledin et al., Sep., 1981, "Isolation and Properties of DNA Polymerase From the Extremely Thermophilic Bacterium *Thermus flavus*" in Biochemistry, a Translation of Biokhimrya 46(9):1576–1584.
Wallace et al., 1981, "A set of Synthetic Oligodeoxyribonucleotide Primers for DNA Sequencing in the Plasmid Vector pBR322" Gene 16:21–26.
Winter et al., 1981, "The Use of Synthetic Oligodeoxynucleotide Primers in Cloning and Sequencing Segment 8 of Influenza Virus (A/PR/8/34)" Nucleic Acids Research 9(2):237–245.

(List continued on next page.)

*Primary Examiner*—James Martinell
*Attorney, Agent, or Firm*—Douglas A. Petry

[57] ABSTRACT

The present invention is directed to a process for amplifying any target nucleic acid sequence contained in a nucleic acid or mixture thereof using a thermostable enzyme. The process comprises treating separate complementary strands of the nucleic acid with a molar excess of two oligonucleotide primers, extending the primers with a thermostable enzyme to form complementary primer extension products which act as templates for synthesizing the desired nucleic acid sequence, and detecting the sequence so amplified. The steps of the reaction can be repeated as often as desired and involve temperature cycling to effect hybridization, promotion of activity of the enzyme, and denaturation of the hybrids formed.

7 Claims, No Drawings

OTHER PUBLICATIONS

Research Awards Index, Fiscal Year 1981, p. 1666, Publication No. (NIH) 82–200.

Kaledin et al., Nov., 1982, "Isolation and Properties of DNA Polymerase From the Extremely Thermophilic Bacterium *Thermus ruber*" in Biochemistry, a Translation of Biokhimiya 47(11):1785–1791.

Okayama and Berg, Feb., 1982, "High–Efficiency Cloning of Full–Length cDNA" Molecular and Cellular Biology 2(2):161–170.

Hong, 1982, "Sequencing of Large Double–Stranded DNA Using the Dideoxy Sequencing Technique" Bioscience Reports 2:907–912.

Rossi et al., Aug., 1982, "An Alternate Method for Sythesis of Double–Stranded DNA Segments" J. Biological Chemistry 257(16):9226–9229.

Conner et al., Jan., 1983, "Detection of Sickle Cell Beta–S Globin Allele by Hybridization With Synthetic Oligonucleotides" Proc. Natl. Acad. Sci. 80:278–282.

Das et al., Mar., 1983, "Use of Synthetic Oligonucleotide Probes Complementary to Genes for Human HLA–DR alpha and beta as Extension Primers for the Isolation of 5'–Specific Genome Clones" Proc. Natl. Acad. Sci. 80:1531–1535.

Deininger, 1983, "Approaches to Rapid DNA Sequence Analysis" Analytical Biochemistry 135:247–263.

Molecular Biological's catalog from Pharmacia, 1984, p. 49.

Schold et al., 1984, "Laboratory Methods Oligonucleotide–Directed Mutagenesis Using Plasmid DNA Templates and Two Primers" DNA 3(6):469–477.

Zoller et al., 1984, "Oligonucleotide–Directed Mutagenesis: A Simple Method Using Two Oligonucleotide Primers and a Single–Stranded DNA Template" DNA 3(6):479–488.

Chen and Seeburg, 1985, "Supercoil Sequencing: A Fast and Simple Method for Sequencing Plasmid DNA" DNA 4(2):165–170.

Ruttiman et al., 1985, "DNA Polymerases From the Extremely Thermophilic Bacterium *Thermus Thermophilus* HB–8" Eur. J. Biochem. 149:41–46.

Zagursky et al., 1985, "Rapid and Easy Sequencing of Large Linear Double–Stranded DNA and Supercoiled Plasmid DNA" Gene Anal Techn. 2:89–94.

Templeton, 1992, "The Polymerase Chain Reaction—History, Methods, and Applications" Diagnostic Molecular Pathology 1(1):58–72.

Khorana Research Proposal, National Science Foundation (1972) (Trial Exhibit A–17).

Putative Kleppe Lecture from 1969 Gordon Conference.

Boehringer Mannheim Product Catalogue, Jan., 1985, pp. IV, 15 and 17.

NCI Grant Application CA No. 11981–01 for Apr. 1, 1970, to Mar. 31, 1975, submitted by Dr. Khorana.

Goeddel et al., 1980, "Synthesis of Human Fibroblast Interferon by *E. coli*" Nucleic Acids Research 8(18):4057–4073.

Houghton et al., 1990, "The Amino–Terminal Sequence of Human Fibroblast Interferon as Deduced From Reverse Transcripts Obtained Using Synthetic Oligonucleotide Primers" Nucleic Acids Research 8(9):1913–1931.

Derynck et al., Aug., 1984, "Human Transforming Growth Factor—Alpha Precurson Structure and Expression in *E. coli*" Cell 38:287–297.

Itakura et al., 1984, "Synthesis and Use of Synthetic Oligonucleotides" Ann. Rev. Biochem. 53:323–356.

Wood et al., 1984, "Expression of Active Human Factor VIII From Recombinant DNA Clones" Nature 312:330–337.

Aug., 1985, Promega Notes 2:1–8.

Saiki et al., Dec., 1985, "Enzymatic Amplification of Beta- -Globin Genomic Sequences and Restriction Site Analysis for Diagnosis of Sickle Cell Anemia" Science 23:1350–1354.

Southern, 1975, "Detection of Specific Sequences Among DNA Fragments Separated by Gel Electrophoresis" J. Mol. Biol. 98:503–517.

Britten and Kohne, Aug., 1968, "Repeated Sequences in DNA" Science 161(3841):529–540.

Wetmur and Davidson, 1968, "Kinetics of Renaturation of DNA" J. Mol. Biol. 31:349–370.

Kochetkov and Budovskii, Oganic Chemistry of Nucleic Acids, London and New York, Plenum Press, 1971, Chapter 4, Entitled "The Secondary Structure of Nucleic Acids" pp. 224–226.

Summers et al., Nov., 1975, "Genome of Hepatitis B Virus: Restriction Enzyme Cleavage and Structure of DNA Extracted from Dane Particles" Proc. Natl. Acad. Sci. USA 72(11):4597–4601.

Chien et al., Sep., 1976, "Deoxyribonucleic Acid Polymerase From the Extreme Thermophile *Thermus aquaticus*" J. Bacteriology 127(3):1550–1557.

Gait and Sheppard, Dec., 1976, "A Polyamide Support for Oligonucleotide Synthesis" J. American Chemical Society 98(26):8514–8516.

Sanger et al., Dec., 1977, "DNA Sequencing with Chain- -Terminating Inhibitors" Proc. Natl. Acad. Sci. USA 74(12):5463–5467.

Kuhn et al., 1978, "DNA Helicases" CSH–Quantitative Biology 43:63–67.

Lehninger, Biochemistry, 2nd ed., New York, NY, Worth Publishers, Inc., 1979, Chapter 32, entitled "Replication and Transcription DNA" pp. 897–899, 904, and 905.

Caton and Robertson, 1979, "New Procedure for the Production of Influenza Virus–Specific Double–Stranded DNA's " Nucleic Acids Research 7(6):1445–1455.

Alvarado–Urbina et al., 1979, "Automated Synthesis of Gene Fragments" Science 214:270–274.

Kaledin et al., Apr., 1980, "Isolation and Properties of DNA Polymerase From Extremely Thermophilic Bacterium *Thermus aquaticus* YT1" 45(4):644–651 in Biochemistry, a Translation.

Suggs et al., Nov., 1981, "Use of Synthetic Oligonucleotides as Hybridization Probes: Isolation of Cloned cDNA Sequences for Human Beta–2–Microglobulin " Proc. Natl. Acad. Sci. USA 78(11):6613–6617

Sambrook et al., 1982, Molecular Cloning, pp. 310–328.

Loeb and Kunkel, 1982, "Fidelity of DNA Synthesis" Ann. Rev. Biochem. 52: 436–437.

Hu and Messing, 1982, "The Making of Strand–Specific M13 Probes" Gene 17:271–277.

Watson et al., Recombinant DNA a Short Course, New York, W.H. Freeman and Company, 1983, p. 41.

Kidd et al., 1983, "Alpha–1–Antitrypsin Deficiency Detection by Direct Analysis of the Mutation in the Gene" Nature 304:230–234.

Sambrook et al., Molecular Cloning, p. 14.2, 1989.

Hunkapiller et al., Jul., 1984, "A Microchemical Facility for the Analysis and Synthesis of Genes and Proteins" Nature 310:105–111.

Gait, Oligonucleotide Synthesis, Cambridge, England, IRL Press Limited, 1984, pp. 9 and 10.

Bahl et al., 1984, "Oligonucleotide Synthesis and Its Applications to Recombinant DNA Technology" Biochemical and Biophysical Studies, pp. 183–197.

Reyes and Wallace, 1984, "Use of Synthetic Oligonucleotide Hybridization Probes for the Characterization and Isolation of Cloned DNAs" Genetic Engineering Principles and Methods 6:157–173.

Ashley and MacDonald, 1984, "Synthesis of Single–Stranded Hybridization Probes from Reusable DNA Templates Bound to Solid Support" Analytical Biochemistry 140:95–103.

Wallace et al., 1985, "Application of Synthetic Oligonucleotides to the Diagnosis of Human Genetic Diseases" Biochimie 67:755–762.

VanBrunt, Sep., 1985, "The New Generation of DNA Synthesizers" Bio/Technology 3(9):775–782.

Pharmacia P–L Biochemicals 1984 Product Reference Guide, Pharmacia P–L Biochemicals, 1984, p. 32.

Bethesda Research Laboratories, Inc. 1979 Catalog, p. 20.

New England Bioloabs 1979 Catalog, pp. 42–45.

Pharmacia Catalog, 1984, pp. 47–49, 83–85.

New England Nuclear—Dupont Catalog, 1983, pp. 134–135.

KITS FOR AMPLIFYING AND DETECTING NUCLEIC ACID SEQUENCES, INCLUDING A PROBE

This application is a divisional application of U.S. Ser. No. 07/546,257, filed Jun. 28, 1990, now abandoned, which in turn is a divisional application of U.S. Ser. No. 07/063, 647, filed Jun. 17, 1987, which issued as U.S. Pat. No. 4,965,188, which is a continuation-in-part application of U.S. Ser. No. 06/899,513 filed Aug. 22, 1986, now abandoned, which is a continuation-in-part of U.S. Ser. No. 06/839,331 filed Mar. 13, 1986, now abandoned and a continuation in part U.S. Ser. No. 06/828,144 filed Feb. 7, 1986 which issued as U.S. Pat. No. 4,683,195, which is a continuation-in-part application of U.S. Ser. No. 06/824,044 filed Jan. 30, 1986, now abandoned, which is a divisional application of U.S. Ser. No. 06/791,308 filed Oct. 25, 1985, which issued as U.S. Pat. No. 4,683,202 which is a continuation-in-part application of U.S. Ser. No. 06/716,975 filed Mar. 28, 1985, now abandoned; and this application is also related to U.S. Ser. No. 833,368 filed Feb. 25, 1986, now abandoned U.S. Ser. No. 899,061 filed Aug. 22, 1986, now abandoned in favor of divisional application U.S. Ser. No. 07/494,174, filed Mar. 14, 1990, which issued as U.S. Pat. No. 5,038,852, U.S. Ser. No. 899,344 filed Aug. 22, 1986, now abandoned in favor of continuation application U.S. Ser. No. 07/491,210, filed Mar. 9, 1990, U.S. Ser. No. 07/063,509, filed Jun. 17, 1987, which issued as U.S. Pat. No. 4,889,818 U.S. Ser. No. 818,127 filed Jan. 10, 1986, now abandoned and U.S. Ser. No. 899,512 filed Aug. 22, 1986 now abandoned.

BACKGROUND OF THE INVENTION

FIELD OF THE INVENTION

The present invention relates to a process for amplifying existing nucleic acid sequences if they are present in a test sample and detecting them if present by using a probe. More specifically, it relates to a process for producing any particular nucleic acid sequence from a given sequence of DNA or RNA in amounts which are large compared to the amount initially present so as to facilitate detection of the sequences, using a thermostable enzyme to catalyze the reaction. The DNA or RNA may be single- or double-stranded, and may be a relatively pure species or a component of a mixture of nucleic acids. The process of the invention utilizes a repetitive reaction to accomplish the amplification of the desired nucleic acid sequence.

DESCRIPTION OF RELATED DISCLOSURES

For diagnostic applications in particular, the target nucleic acid sequence may be only a small portion of the DNA or RNA in question, so that it may be difficult to detect its presence using nonisotopically labeled or end-labeled oligonucleotide probes. Much effort is being expended in increasing the sensitivity of the probe detection systems, but little research has been conducted on amplifying the target sequence so that it is present in quantities sufficient to be readily detectable using currently available methods.

Several methods have been described in the literature for the synthesis of nucleic acids de novo or from an existing sequence. These methods are capable of producing large amounts of a given nucleic acid of completely specified sequence.

One known method for synthesizing nucleic acids de novo involves the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared which can then be joined together to form longer nucleic acids. For a description of this method, see Narang, S. A., et al., *Meth. Enzymol.*, 68, 90 (1979) and U.S. Pat. No. 4,356,270. The patent describes the synthesis and cloning of the somatostatin gene.

A second type of organic synthesis is the phosphodiester method, which has been utilized to prepare a tRNA gene. See Brown, E. L., et al., *Meth. Enzymol.*, 68, 109 (1979) for a description of this method. As in the phosphotriester method, the phosphodiester method involves synthesis of oligonucleotides which are subsequently joined together to form the desired nucleic acid.

Although the above processes for de novo synthesis may be utilized to synthesize long strands of nucleic acid, they are not very practical to use for the synthesis of large amounts of a nucleic acid. Both processes are laborious and time-consuming, require expensive equipment and reagents, and have a low overall efficiency. The low overall efficiency may be caused by the inefficiencies of the synthesis of the oligonucleotides and of the joining reactions. In the synthesis of a long nucleic acid, or even in the synthesis of a large amount of a shorter nucleic acid, many oligonucleotides would need to be synthesized and many joining reactions would be required. Consequently, these methods would not be practical for synthesizing large amounts of any desired nucleic acid.

Methods also exist for producing nucleic acids in large amounts from small amounts of the initial existing nucleic acid. These methods involve the cloning of a nucleic acid in the appropriate host system, where the desired nucleic acid is inserted into an appropriate vector which is used to transform the host. When the host is cultured the vector is replicated, and hence more copies of the desired nucleic acid are produced. For a brief description of subcloning nucleic acid fragments, see Maniatis, T., et al., *Molecular Cloning: A Laboratory Manual*, Cold Spring Harbor Laboratory, pp. 390–401 (1982). See also the techniques described in U.S. Pat. Nos. 4,416,988 and 4,403,036.

A third method for synthesizing nucleic acids, described in U.S. Pat. No. 4,293,652, is a hybrid of the above-described organic synthesis and molecular cloning methods. In this process, the appropriate number of oligonucleotides to make up the desired nucleic acid sequence is organically synthesized and inserted sequentially into a vector which is amplified by growth prior to each succeeding insertion.

The present invention bears some similarity to the molecular cloning method; however, it does not involve the propagation of any organism and thereby avoids the possible hazards or inconvenience which this entails. The present invention also does not require synthesis of nucleic acid sequences unrelated to the desired sequence, and thereby the present invention obviates the need for extensive purification of the product from a complicated biological mixture.

European Pat. Publication No. 200,362 published Dec. 10, 1986 discloses a procedure whereby existing nucleic acids may be produced in larger quantities so as to prepare other nucleic acids or to diagnose for the presence of nucleic acids. The amplification and detection process is also described by Saiki et al., *Science*, 230:1350–1354 (1985), and by Saiki et al., *Biotechnology*, 3:1008–1012 (1985). U.S. Ser. No. 899,061 filed Aug. 22, 1986, supra, now abandoned in favor of divisional application U.S. Ser. No. 07/494,174, filed Mar. 14, 1990, which issued as U.S. Pat. No. 5,038,852, discloses carrying out an amplification of nucleic acids in the presence of a thermostable enzyme in a heat-conducting block whose temperature is controlled by computer means. U.S. application Ser. No. 899,344 filed Aug. 22, 1986, supra, now abandoned in favor of continuation application U.S. Ser. No. 07/491,210, filed Mar. 9, 1990 discloses an amplification procedure followed by dot blot analysis using a heat-stable enzyme. U.S. application Ser. No. 899,241 filed Aug. 22, 1986, supra, now abandoned, discloses purification of a thermostable enzyme, preferably a polymerase from *Thermus aquaticus*.

SUMMARY OF THE INVENTION

The present invention resides in a process for amplifying one or more specific nucleic acid sequences present in a nucleic acid or mixture thereof using primers and a thermostable enzyme. The extension product of one primer when hybridized to the other becomes a template for the production of the desired specific nucleic acid sequence, and vice versa, and the process is repeated as often as is necessary to produce the desired amount of the sequence. The method herein improves the specificity of the amplification reaction, resulting in a very distinct signal of amplified nucleic acid. In addition, the method herein eliminates the need for transferring reagents from one vessel to another after each amplification cycle. Such transferring is not required because the thermostable enzyme will withstand the high temperatures required to denature the nucleic acid strands and therefore does not need replacement. The temperature cycling may, in addition, be automated for further reduction in manpower and steps required to effectuate the amplification reaction.

More specifically, the present invention provides a process for amplifying at least one specific nucleic acid sequence contained in a nucleic acid or a mixture of nucleic acids, wherein if the nucleic acid is double-stranded, it consists of two separated complementary strands of equal or unequal length, which process comprises:

(a) contacting each nucleic acid strand with four different nucleoside triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand;

(b) contacting each nucleic acid strand, at the same time as or after step (a), with a thermostable enzyme which enables combination of the nucleoside triphosphates to form primer extension products complementary to each strand of each nucleic acid;

(c) maintaining the mixture from step (b) at an effective temperature for an effective time to activate the enzyme, and to synthesize, for each different sequence being amplified, an extension product of each primer which is complementary to each nucleic acid strand template, but not so high (a temperature) as to separate each extension product from its complementary strand template;

(d) heating the mixture from step (c) for an effective time and at an effective temperature to separate the primer extension products from the templates on which they were synthesized to produce single-stranded molecules, but not so high (a temperature) as to denature irreversibly the enzyme;

(e) cooling the mixture from step (d) at an effective temperature for an effective time to promote hybridization of each primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d), but not so high (a temperature) as to separate each extension product from its complementary strand template, wherein steps (e) and (f) are carried out simultaneously or sequentially.

The steps (d), (e) and (f) may be repeated until the desired level of sequence amplification is obtained. The preferred thermostable enzyme herein is a polymerase extracted from *Thermus aquaticus* (Taq polymerase). Most preferably, if the enzyme is Taq polymerase, in step (a) the nucleic acid strands are contacted with a buffer comprising about 1.5–2 mM of a magnesium salt, 150–200 $\mu$M each of the nucleotides, and 1 $\mu$M of each primer, steps (a), (e) and (f) are carried out at about 45–58° C., and step (d) is carried out at about 90–100° C.

In a preferred embodiment, the nucleic acid(s) are double-stranded and step (a) is accomplished by (i) heating each nucleic acid in the presence of four different nucleoside triphosphates and one oligonucleotide primer for each different specific sequence being amplified, for an effective time and at an effective temperature to denature each nucleic acid, wherein each primer is selected to be substantially complementary to different strands of each specific sequence, such that the extension product synthesized from one primer, when it is separated from its complement, can serve as a template for synthesis of the extension product of the other primer; and (ii) cooling the denatured nucleic acids to a temperature which promotes hybridization of each primer to its complementary nucleic acid strand.

In other embodiments the invention relates to a process for detecting the presence or absence of at least one specific nucleic acid sequence in a sample containing a nucleic acid or mixture of nucleic acids, or distinguishing between two different sequences in said sample, wherein the sample is suspected of containing said sequence or sequences, and wherein if the nucleic acid(s) are double-stranded, they each consist of two separated complementary strands of equal or unequal length, which process comprises steps (a) to (f) mentioned above, resulting in amplification in quantity of the specific nucleic acid sequence(s), if present;

(g) adding to the product of step (f) a labeled oligonucleotide probe, for each sequence being detected, capable of hybridizing to said sequence or to a mutation thereof; and (h) determining whether said hybridization has occurred.

In yet another embodiment, the invention relates to a process for detecting the presence or absence of at least one nucleotide variation in sequence in one or more nucleic acids contained in a sample, wherein if the nucleic acid is double-stranded it consists of two separated complementary strands of equal or unequal length, which process comprises steps (a)–(f) mentioned above, wherein steps (d), (e) and (f) are repeated a sufficient number of times to result in detectable amplification of the nucleic acid containing the sequence, if present;

(g) affixing the product of step (f) to a membrane;

(h) treating the membrane under hybridization conditions with a labeled sequence-specific oligonucleotide probe capable of hybridizing with the amplified nucleic acid sequence only if a sequence of the probe is complementary to a region of the amplified sequence; and (i) detecting whether the probe has hybridized to an amplified sequence in the nucleic acid sample.

If the sample comprises cells, preferably they are heated before step (a) to expose the nucleic acids therein to the reagents. This step avoids extraction of the nucleic acids prior to reagent addition.

In a variation of this process, the primer(s) and/or nucleoside triphosphates are labeled so that the resulting amplified sequence is labeled. The labeled primer(s) and/or nucleoside triphosphate(s) can be present in the reaction mixture initially or added during a later cycle. The sequence-specific oligonucleotide (unlabeled) is affixed to a membrane and treated under hybridization conditions with the labeled amplification product so that hybridization will occur only if the membrane-bound sequence is present in the amplification product.

In yet another embodiment, the invention herein relates to a process for cloning into a cloning vector one or more specific nucleic acid sequences contained in a nucleic acid or a mixture of nucleic acids, which nucleic acid(s) when double-stranded consist of two separated complementary strands, and which nucleic acid(s) are amplified in quantity before cloning, which process comprises steps (a)–(f) mentioned above, with steps (d), (e) and (f) being repeated a sufficient number of times to result in detectable amplification of the nucleic acid(s) containing the sequence(s);

(g) adding to the product of step (f) a restriction enzyme for each of said restriction sites to obtain cleaved products in a restriction digest; and (h) ligating the cleaved product(s) of step (g) containing the specific sequence(s) to be cloned into one or more cloning vectors containing a promoter and a selectable marker.

In a final embodiment, the invention herein relates to a process for cloning into a cloning vector one or more specific nucleic acid sequences contained in a nucleic acid or mixture of nucleic acids, which nucleic acid(s), when double-stranded, consist of two separated complementary strands of equal or unequal length which nucleic acid(s) are amplified in quantity before cloning, which process comprises steps (a)–(f) mentioned above, with steps (d), (e) and (f) being repeated a sufficient number of times to result in effective amplification of the nucleic acid(s) containing the sequence(s) for blunt-end ligation into one or more cloning vectors; and (g) ligating the amplified specific sequence(s) to be cloned obtained from step (f) into one or more of said cloning vectors in the presence of a ligase, said amplified sequence(s) and vector(s) being present in sufficient amounts to effect the ligation.

In a product embodiment, the invention provides a composition of matter useful in amplifying at least one specific nucleic acid sequence contained in a nucleic acid or a mixture of nucleic acids, comprising four different nucleoside triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer.

In another product embodiment, the invention provides a sample of one or more nucleic acids comprising multiple strands of a specific nucleic acid sequence contained in the nucleic acid(s). The sample may comprise about 10–100 of the strands, about 100–1000 of the strands, or over about 1000 of the strands.

In a final product embodiment, the invention provides an amplified nucleic acid sequence from a nucleic acid or mixture of nucleic acids comprising multiple copies of the sequence produced by the amplification processes herein.

DETAILED DESCRIPTION OF THE PREFERRED EMBODIMENTS

The term "oligonucleotide" as used herein is defined as a molecule comprised of two or more deoxyribonucleotides or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of four different nucleoside triphosphates and a thermostable enzyme in an appropriate buffer ("buffer" includes pH, ionic strength, cofactors, etc.) and at a suitable temperature. For Taq polymerase, the buffer herein preferably contains 1.5–2 mM of a magnesium salt, preferably $MgCl_2$, 150–200 $\mu$M of each nucleotide, and 1 $\mu$M of each primer, along with preferably 50 mM KCl, 10 mM Tris buffer at pH 8–8.4, and 100 $\mu$g/ml gelatin.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature and source of primer and use of the method. For example, depending on the complexity of the target sequence, the oligonucleotide primer typically contains 15–25 or more nucleotides, although it may contain more or fewer nucleotides. Short primer molecules generally require lower temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

As used herein, the terms "restriction endonucleases" and "restriction enzymes" refer to bacterial enzymes each of which cut double-stranded DNA at or near a specific nucleotide sequence.

As used herein, the term "DNA polymorphism" refers to the condition in which two or more different nucleotide sequences can exist at a particular site in DNA.

As used herein, the term "nucleotide variation in sequence" refers to any single or multiple nucleotide substitutions, deletions or insertions. These nucleotide variations may be mutant or polymorphic allele variations. Therefore, the process herein can detect single nucleotide changes in nucleic acids such as occur in β-globin genetic diseases caused by single-base mutations, additions or deletions (some β-thalassemias, sickle cell anemia, hemoglobin C disease, etc.), as well as multiple-base variations such as are involved with α-thalassemia or some β-thalassemias. In addition, the process herein can detect polymorphisms, which are not necessarily associated with a disease, but are merely a condition in which two or more different nucleotide sequences (whether having substituted, deleted or inserted nucleotide base pairs) can exist at a particular site in the nucleic acid in the population, as with HLA regions of the human genome and random polymorphisms such as mitochondrial DNA. The polymorphic sequence-specific oligonucleotide probes described in detail hereinafter may be used to detect genetic markers linked to a disease such as insulin-dependent diabetis mellitus or in forensic applications. If the nucleic acid is double-stranded, the nucleotide variation in sequence becomes a base pair variation in sequence.

The term "sequence-specific oligonucleotides" refers to oligonucleotides which will hybridize to specific sequences whether or not contained on alleles, which sequences span the base pair variation being detected and are specific for the sequence variation being detected. Depending on the sequences being analyzed, one or more sequence-specific nucleotides may be employed for each sequence, as described further hereinbelow.

As used herein, the term "restriction fragment length polymorphism" ("RFLP") refers to the differences among individuals in the lengths of restriction fragments formed by digestion with a particular restriction endonuclease.

As used herein, the term "thermostable enzyme" refers to an enzyme which is stable to heat and is heat resistant and catalyzes (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis terminates, producing molecules of different lengths. There may be thermostable enzymes, however, which initiate synthesis at the 5' end and proceed in the other direction, using the same process as described above.

The thermostable enzyme herein must satisfy a single criterion to be effective for the amplification reaction of this invention, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90 to about 105° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversibly denatured at about 90–100° C.

The thermostable enzyme herein preferably has an optimum temperature at which it functions which is higher than about 40° C., which is the temperature below which hybridization of primer to template is promoted, although, depending on (1) magnesium and salt concentrations and (2) composition and length of primer, hybridization can occur at higher temperatures (e.g., 45–70° C.). The higher the temperature optimum for the enzyme, the greater the specificity and/or selectivity of the primer-directed extension process. However, enzymes that are active below 40° C., e.g., at 37° C., are also within the scope of this invention, provided they are heat-stable. Preferably, the optimum temperature ranges from about 50 to 80° C., more preferably 60–80° C.

Examples of enzymes which have been reported in the literature as being resistant to heat include heat-stable polymerases, such as, e.g., polymerases extracted from the thermostable bacteria *Thermus flavus, Thermus ruber, Thermus thermophilus, Bacillus stearothermophilus* (which has a somewhat lower temperature optimum than the others listed), *Thermus aquaticus, Thermus lacteus, Thermus rubens*, and *Methanothermus fervidus*.

The preferred thermostable enzyme herein is a DNA polymerase isolated from *Thermus aquaticus*, strain YT-1, and purified as described in U.S. application Ser. No. 899,241 filed Aug. 22, 1986, now abandoned the disclosure of which is incorporated herein by reference. Briefly, *Thermus aquaticus* cells are grown and the polymerase is isolated and purified from the crude extract using the first five steps indicated by Kaledin et al., *Biokhimiya*, 45, 644–651 (1980), the disclosure of which is incorporated herein by reference. During the fifth step (DEAE column at pH 7.5), an assay is made for contaminating endo/exonucleases and only those fractions with polymerase activity and minimal nuclease contamination are pooled. The last chromatographic purification step uses a phosphocellulose column suggested by Chien et al., *J. Bacteriol.*, 127:1550–1557 (1976), the disclosure of which is incorporated herein by reference. Nuclease(s) and polymerase activities are assayed as described above, and only those polymerase fractions with minimal nuclease contamination are pooled.

While Kaledin et al. and Chien et al. report a purified enzyme with a molecular weight of 62–63 kdaltons, data using the modified purification protocol described above suggest a molecular weight of about 86–90 kdaltons.

The thermostable enzyme may be produced by recombinant DNA techniques by the method described in U.S. Ser. No. 07/063,509, filed Jun. 17, 1987, which issued as U.S. Pat. No. 4,889,818, entitled "Purified Thermostable Enzyme", to Gelfand et al., the disclosure of which is incorporated herein by reference. The thermostable enzyme also may be stored stably in a buffer as described in that same U.S. application.

The present invention is directed to a process for amplifying any one or more desired specific nucleic acid sequences contained in or suspected of being in a nucleic acid. Because large amounts of a specific sequence may be produced by this process, the present invention may be used for improving the efficiency of cloning DNA or messenger RNA and for amplifying a target sequence to facilitate detection thereof.

In general, the present process involves a chain reaction for producing, in exponential quantities relative to the number of reaction steps involved, at least one specific nucleic acid sequence given (a) that the ends of the specified sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any nucleic acid, in purified or nonpurified form, can be utilized as the starting nucleic acid or acids, provided it contains or is suspected of containing the specific sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the β-globin gene contained in whole human DNA, or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi or amniotic cells by a variety of techniques such as that described by Maniatis et al., *Molecular Cloning: A Laboratory Manual* (1982), 280–281.

For the process using sequence-specific probes to detect the amplified material, the cells may be directly used without purification of the nucleic acid if they are suspended in hypotonic buffer and heated to about 90–100° C., until cell lysis and dispersion of intracellular components occur, generally 1 to 15 minutes. After the heating step the amplification reagents may be added directly to the lysed cells.

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process.

It will be understood that the word "primer" as used hereinafter may refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the phosphotriester and phosphodiester methods described above, or automated embodiments thereof. In one such automated embodiment diethylphosphoramidites are used as starting materials and may be synthesized as described by Beaucage et al., *Tetrahedron Letters* (1981), 22:1859–1862. One method for synthesizing oligonucleotides on a modified solid support is described in U.S. Pat. No. 4,458,066. It is also possible to use a primer which has been isolated from a biological source (such as a restriction endonuclease digest).

The specific nucleic acid sequence is produced by using the nucleic acid containing that sequence as a template. The first step involves contacting each nucleic acid strand with four different nucleoside triphosphates and one oligonucleotide primer for each different nucleic acid sequence being amplified or detected. If the nucleic acids to be amplified or detected are DNA, then the nucleotide triphosphates are dATP, dCTP, dGTP and TTP.

The nucleic acid strands are used as a template for the synthesis of additional nucleic acid strands. This synthesis can be performed using any suitable method. Generally it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Preferably, the concentration of nucleoside triphosphates is 150–200 $\mu$M each in the buffer for amplification, and MgCl is present in the buffer in an amount of 1.5–2 mM to increase the efficiency and specificity of the reaction.

The resulting solution is then treated according to whether the nucleic acids being amplified or detected are double or single-stranded. If the nucleic acids are single-stranded, then no denaturation step need by employed, and the reaction mixture is held at a temperature which promotes hybridization of the primer to its complementary target (template) sequence. Such temperature is generally from about 35 to 65° C. or higher, preferably 37–60° C., for an effective time, generally one-half to five minutes, preferably one-three minutes. Preferably, 45–58° C. is used for Taq polymerase and >15-mer primers to increase the specificity of primer hybridization. Shorter primers need lower temperatures.

The complement to the original single-stranded nucleic acid may be synthesized by adding one or two oligonucleotide primers thereto. If an appropriate single primer is added, a primer extension product is synthesized in the presence of the primer, the thermostable enzyme and the nucleoside triphosphates. The product will be partially complementary to the single-stranded nucleic acid and will hybridize with the nucleic acid strand to form a duplex of strands of unequal length which may then be separated into single strands as described above to produce two single separated complementary strands. Alternatively, two appropriate primers may be added to the single-stranded nucleic acid and the reaction carried out.

If the nucleic acid contains two strands, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90 to 105° C. for times generally ranging from about 0.5 to 5 minutes. Preferably the effective denaturing temperature is 90–100° C. for 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSH-Quantitative Biology,* 43:63 (1978), and techniques for using RecA are reviewed in C. Radding, *Ann. Rev. Genetics,* 16:405–37 (1982). The denaturation produces two separated complementary strands of equal or unequal length.

If the double-stranded nucleic acid is denatured by heat, the reaction mixture is allowed to cool to a temperature which promotes hybridization of each primer present to its complementary target (template) sequence. This temperature is usually from about 35 to about 65° C. or higher, depending on reagents, preferably from about 37° C. to about 60° C., maintained for an effective time, generally 0.5 to 5 minutes, and preferably 1–3 minutes. In practical terms, the temperature is simply lowered from about 95° C. to about 65° C. or to as low as 37° C., preferably to about 45–58° C. for Taq polymerase, and hybridization occurs at a temperature within this range.

Whether the nucleic acid is single- or double-stranded, the thermostable enzyme may be added at the denaturation step or when the temperature is being reduced to or is in the range for promoting hybridization. The reaction mixture is then heated to a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80° C.–90° C.).

Depending mainly on the types of enzyme and nucleic acid(s) employed, the typical temperature effective for this synthesis reaction generally ranges from about 40 to 80° C., preferably 50–75° C. The temperature more preferably ranges from about 65–75° C. when a polymerase from *Thermus aquaticus* is employed. The period of time required for this synthesis may range from about 0.5 to 40 minutes or more, depending mainly on the temperature, the length of the nucleic acids, the enzyme and the complexity of the nucleic acid mixture, preferably one to three minutes. If the nucleic acid is longer, a longer period of time is generally required. The presence of dimethylsulfoxide (DMSO) is not necessary or recommended because DMSO was found to inhibit Taq polymerase enzyme activity.

The newly synthesized strand and its complementary nucleic acid strand form a double-stranded molecule which is used in the succeeding steps of the process. In the next step, the strands of the double-stranded molecule are separated by heat denaturation at a temperature effective to denature the molecule, but not so high that the thermostable enzyme is completely and irreversibly denatured or inactivated. Depending mainly on the type of enzyme and the length of nucleic acid, this temperature generally ranges from about 90 to 105° C., more preferably 90–100° C., and the time for denaturation typically ranges from 0.5 to four minutes, depending mainly on the temperature and the nucleic acid length.

After this time, the temperature is decreased to a level which promotes hybridization of the primer to its complementary single-stranded molecule (template) produced from the previous step. Such temperature is described above.

After this hybridization step, or in lieu of (or concurrently with) this hybridization step, the temperature is adjusted to a temperature which is effective to promote the activity of the thermostable enzyme to enable synthesis of a primer extension product using as template the newly synthesized strand from the previous step. The temperature again must not be so high as to separate (denature) the extension product from its template, as previously described (usually from 40 to 80° C. for 0.5 to 40 minutes, preferably 50 to 70° C. for 1–3 minutes). Hybridization may occur during this step, so that the previous step of cooling before denaturation is not required. In such a case, using simultaneous steps, the preferred temperature range is 50° C.–70° C.

The heating and cooling steps of strand separation, hybridization, and extension product synthesis can be repeated as often as needed to produce the desired quantity of the specific nucleic acid sequence, depending on the ultimate use. The only limitation is the amount of the primers, the thermostable enzyme and the nucleotide triphosphates present. Preferably, the steps are repeated at least once. For use in detection, the number of cycles will depend, e.g., on the nature of the sample. For example, fewer cycles will be required if the sample being amplified is pure. If the sample is a complex mixture of nucleic acids, more cycles will be required to amplify the signal sufficiently for its detection. For general amplification and detection, preferably the process is repeated at least 20 times.

When labeled sequence-specific probes are employed as described below, preferably the steps are repeated at least five times. When human genomic DNA is employed with such probes, the process is repeated preferably 15–30 times to amplify the sequence sufficiently that a clearly detectable signal is produced, i.e., so that background noise does not interfere with detection.

As will be described in further detail below, the amount of the specific nucleic acid sequence produced will accumulate in an exponential fashion.

No additional nucleotides, primers, or thermostable enzyme need be added after the initial addition, provided that the enzyme has not become denatured or inactivated irreversibly, in which case it is necessary to replenish the enzyme after each denaturing step. Addition of such materials at each step, however, will not adversely affect the reaction.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

After the appropriate length of time has passed to produce the desired amount of the specific nucleic acid sequence, the reaction may be halted by inactivating the enzymes in any known manner (e.g., by adding EDTA, $CHCl_3$, SDS or phenol) or by separating the components of the reaction.

The process of the present invention may be conducted continuously. In one embodiment of an automated process, the reaction mixture may be temperature cycled such that the temperature is programmed to be controlled at a certain level for a certain time.

One such instrument for this purpose is the automated machine for handling the amplification reaction of this invention described in U.S. Ser. No. 833,368 filed Feb. 25, 1986 now abandoned, entitled "Apparatus And Method For Performing Automated Amplification of Nucleic Acid Sequences And Assays Using Heating And Cooling Steps," the disclosure of which is incorporated herein by reference. Briefly, this instrument utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence(s) to be amplified plus the nucleotide triphosphates and primers. The computer includes a user interface through which a user can enter process parameters which control the characteristics of the various steps in the amplification sequence such as the times and temperatures of incubation, the amount of enzyme to transfer, etc.

A preferred machine which may be employed utilizes temperature cycling without a liquid handling system because the enzyme need not be transferred at every cycle. Such a machine is described more completely in U.S. application Ser. No. 899,061 filed Aug. 22, 1986, now abandoned in favor of divisional application U.S. Ser. No. 07/494,174, filed Mar. 14, 1990, which issued a U.S. Pat. No. 5,038,852 the disclosure of which is incorporated herein by reference. Briefly, this instrument consists of the following systems:

1. A heat-conducting container for holding a given number of tubes, preferably 500 µl tubes, which contain the reaction mixture of nucleotide triphosphates, primers, nucleic acid sequences, and enzyme.

2. A means to heat, cool, and maintain the heat-conducting container above and below room temperature, which means has an input for receiving a control signal for controlling which of the temperatures at or to which the container is heated, cooled or maintained. (This may be Peltier heat pumps available from Materials Electronics Products Corporation in Trenton, N.J. or a water heat exchanger.)

3. A computer means (e.g., a microprocessor controller), coupled to the input of said means, to generate the signals which control automatically the amplification sequence, the temperature levels, and the temperature ramping and timing.

In another embodiment, the enzyme used for the synthesis of primer extension products can be immobilized in a column. The other reaction components can be continuously circulated by a pump through the column and a heating coil in series. Thus, the nucleic acids produced can be repeatedly denatured without inactivating the enzyme.

The present invention is demonstrated diagrammatically below where double-stranded DNA containing the desired sequence [S] comprised of complementary strands [$S^+$] and [$S^-$] is utilized as the nucleic acid. During the first and each subsequent reaction cycle extension of each oligonucleotide primer on the original template will produce one new ssDNA molecule product of indefinite length which terminates with only one of the primers. These products, hereafter referred to as "long products," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence [$S^+$] or [S]. These molecules will also function as templates for one or the other of the oligonucleotide primers, producing further [$S^+$] and [$S^-$], and thus a chain reaction can be sustained which will result in the accumulation of [S] at an exponential rate relative to the number of cycles.

By-products formed by oligonucleotide hybridizations other than those intended are not self-catalytic (except in rare instances) and thus accumulate at a linear rate.

The specific sequence to be amplified, [S], can be depicted diagrammatically as:

$S^+$] 5' AAAAAAAAAAXXXXXXXXXXXCCCCCCCCCC 3'

[$S^-$] 3' TTTTTTTTTTYYYYYYYYYYGGGGGGGGGG 5'

The appropriate oligonucleotide primers would be:

Primer 1: GGGGGGGGGG

Primer 2: AAAAAAAAAA so that if DNA containing [S]

```
....zzzzzzzzzzzzzzzz-
      zAAAAAAAAAAXXXXXXXXXXC-
      CCCCCCCCCzzzzzzzzzzzzzzz.....

....zzzzzzzzzzzzzzzzTTTTTTTT-
      TYYYYYYYYYYGGGGGGGGGGzzzzzzzzzzzzzzzz.....
``` is separated into single strands and its single strands are hybridized to Primers 1 and 2, the following extension reactions can be catalyzed by a thermostable polymerase in the presence of the four nucleoside triphosphates:

```
                                              3'        5'
              extends ←------------------- GGGGGGGGGG  Primer 1
    ....zzzzzzzzzzzzzzzzAAAAAAAAAAXXXXXXXXXXCCCCCCCCCCzzzzzzzzzzzzzzzz....
    original template strand⁺ original template strand⁻
```

```
                              -continued
....zzzzzzzzzzzzzzzzTTTTTTTTTTYYYYYYYYYYGGGGGGGGGGzzzzzzzzzzzzzzzz....
        Primer 2         AAAAAAAAAA-------------->extends
                         5'        3'
```

On denaturation of the two duplexes formed, the products are:

```
3'                                                        5'
....zzzzzzzzzzzzzzzzTTTTTTTTTTYYYYYYYYYYGGGGGGGGGG
newly synthesized long product 1

5'                                                                      3'
....zzzzzzzzzzzzzzzzAAAAAAAAAAXXXXXXXXXXCCCCCCCCCCzzzzzzzzzzzzzzzz....
original template strand⁺

3'                                                                      5'
....zzzzzzzzzzzzzzzzTTTTTTTTTTYYYYYYYYYYGGGGGGGGGGzzzzzzzzzzzzzzzz....
original template strand⁻

5'                                                 3'
                     AAAAAAAAAAXXXXXXXXXXCCCCCCCCCCzzzzzzzzzzzzzzzz....
                     newly synthesized long product 2
```

If these four strands are allowed to rehybridize with Primers 1 and 2 in the next cycle, the thermostable polymerase will catalyze the following reactions:

```
      Primer 2       5'  AAAAAAAAAA------------------->extends to here
3'....zzzzzzzzzzzzzzzzTTTTTTTTTTYYYYYYYYYYGGGGGGGGGG 5'
newly synthesized long product 1 extends<--------------------------GGGGGGGGGG 5' Primer 1

5'....zzzzzzzzzzzzzzzzAAAAAAAAAAXXXXXXXXXXCCCCCCCCCCzzzzzzzzzzzzzzzz....3'
original template strand⁺

Primer 2       5'  AAAAAAAAAA--------------------------->extends
3'....zzzzzzzzzzzzzzzzTTTTTTTTTTYYYYYYYYYYGGGGGGGGGGzzzzzzzzzz....5'
original template strand⁻ extends to here<-------------------GGGGGGGGGG  5'  Primer 1

5' AAAAAAAAAAXXXXXXXXXXCCCCCCCCCCzzzzzzzzzzzzzzzz..3'
                 newly synthesized long product 2
```

If the strands of the above four duplexes are separated, the following strands are found:

```
                     5' AAAAAAAAAAXXXXXXXXXXCCCCCCCCCC 3'
                        newly synthesized [S⁺]

3'....zzzzzzzzzzzzzzzzzzTTTTTTTTTTYYYYYYYYYYGGGGGGGGGG 5'
first cycle synthesized long product 1

3'....zzzzzzzzzzzzzzzzzzTTTTTTTTTTYYYYYYYYYYGGGGGGGGGG 5'
newly synthesized long product 1

5'....zzzzzzzzzzzzzzzzzzAAAAAAAAAAXXXXXXXXXXCCCCCCCCCCzzzzzzzz....3'
original template strand⁺

5' AAAAAAAAAAXXXXXXXXXXCCCCCCCCCCzzzzzzzzzzzzzzzz...3'
                 newly synthesized long product 2

3'..zzzzzzzzzzzzzzzzTTTTTTTTTTYYYYYYYYYYGGGGGGGGGGzzzzzzzzzzzzzzzz...3'
original template strand⁻
```

```
                           -continued
        3' TTTTTTTTTTTYYYYYYYYYYGGGGGGGGGG 5'
           newly synthesized [S⁻]

5' AAAAAAAAAAXXXXXXXXXXCCCCCCCCCCzzzzzzzzzzzzzzzz...3'
           first cycle synthesized long product 2
```

It is seen that each strand which terminates with the oligonucleotide sequence of one primer and the complementary sequence of the other is the specific nucleic acid sequence [S] that is desired to be produced.

The amount of original nucleic acid remains constant in the entire process, because it is not replicated. The amount of the long products increases linearly because they are produced only from the original nucleic acid. The amount of the specific sequence increases exponentally. Thus, the specific sequence will become the predominant species. This is illustrated in the following table, which indicates the relative amounts of the species theoretically present after n cycles, assuming 100% efficiency at each cycle:

| | Number of Double Strands After 0 to n Cycles | | |
|---|---|---|---|
| Cycle Number | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n - n - 1)$ |

When a single-stranded nucleic acid is utilized as the template, only one long product is formed per cycle.

A sequence within a given sequence can be amplified after a given number of amplifications to obtain greater specificity of the reaction by adding after at least one cycle of amplification a set of primers which are complementary to internal sequences (which are not on the ends) of the sequence to be amplified. Such primers may be added at any stage and will provide a shorter amplified fragment. Alternatively, a longer fragment can be prepared by using primers with non-complementary ends but having some overlap with the primers previously utilized in the amplification.

The method herein may be utilized to clone a particular nucleic acid sequence for insertion into a suitable expression vector. The vector may then be used to transform an appropriate host organism to produce the gene product of the sequence by standard methods of recombinant DNA technology.

The amplification process herein may yield a mixture of nucleic acids, resulting from the original template nucleic acid, the expected target amplified products, and various background non-target products. The amplified product can also be a mixture if the original template DNA contains multiple target sequences, such as in a heterozygous diploid genome or when there is a family of related genes.

The primers herein may be modified to assist the rapid and specific cloning of the mixture of DNAs produced by the amplification reaction. In one such modification, a restriction site is contained in each of the primers or in the sequence to be amplified and cloned. Preferably, the same or different restriction sites are incorporated at the 5' ends of the primers to result in restriction sites at the two ends of the amplified product. When cut with the appropriate enzymes, the amplified product can then be easily inserted into plasmid or vial vectors and cloned. This cloning allows the analysis or expression of individual amplified products, not a mixture.

If the primers have restriction sites incorporated therein, the same restriction site can be used for both primers. The use, however, of different sites allows the insertion of the product into the vector with a specific orientation and suppresses multiple insertions as well as insertions arising from amplifications based on only one of the two primers. The specific orientation is useful when cloning into single-strand sequencing vectors, when single-strand hybridization probes are used, or when the cloned product is being expressed.

One method to prepare the primers is to choose a primer sequence which differs minimally from the target sequence. Regions in which each of the primers is to be located are screened for homology to restriction sites appropriate to the desired vector. For example, the target sequence "CAG-TATCCGA . . . " differs by only one base from one containing a BamHI site. A primer sequence is chosen to match the target exactly at its 3' end, and to contain the altered sequence and restriction site near its 5' end (for example, "CAGgATCCGA . . . ", where the lower case letter symbolizes a mismatch with the target sequence). This minimally altered sequence will not interfere with the ability of the primer to hybridize to the original target sequence and to initiate polymerization. After the first amplification cycle the primer is copied, becomes the target, and matches exactly with new primers.

After the amplification process, the products are cleaved with the appropriate restriction enzymes, the restriction digest is optionally separated from inhibitors of ligation such as the nucleotide triphosphates and salts by, for example, passing over a desalting column, or a molecular weight chromatography column, or through a membrane, and the digestion product(s) containing the amplified sequence to be cloned is/are inserted by ligation into a cloning vector such as bacteriophage M13. The cloning vector generally has a selectable marker and may optionally also have a promoter. The gene may then be sequenced and/or expressed, if it codes for a protein, using well known techniques. The gene may also be sequenced by adding an appropriate primer during the amplification process which primer is complementary to the desired portion which is to be sequenced. The primer will form an extension product, and the extent of amplification with such extension product will provide sequence information.

Another method for preparing the primers involves taking the 3' end of the primers from the target sequence and adding the desired restriction site(s) to the 5' end of the primer. For the above example, a HindIII site could be added to make the sequence "cgaagcttCAGTATCCGA . . . ", where lower case letters are as described above. The added bases would not contribute to the hybridization in the first cycle of amplification, but would match in subsequent cycles. The final amplified products are then cut with restriction enzyme (s) and cloned and expressed as described above. The gene being amplified may be, for example, human beta-hemoglobin or the human HLA DQ, DR or DP-α and -β genes.

In an alternative, but less preferred and less efficient, method of cloning wherein blunt-end ligation is employed rather than sticky-end ligation (using restriction enzymes), the basic amplification procedure is employed without concern for restriction enzymes in the primers or sequence(s) to be cloned. The steps must be repeated sufficiently, however, to produce enough amplified sequence(s) to effect ligation. Blunt-end ligation requires greater concentrations of sequence(s) and cloning vector(s) to be present than sticky-end ligation. In addition, the ligation must take place in the presence of a ligase, such as T4 ligase, E. coli ligase and ligase. Once the amplified product is obtained, the ligation procedure is a standard procedure using conditions well known to those skilled in the art.

The cloning method which does not involve blunt end ligation controls the orientation or multiplicity of insertion of the amplified product into the cloning vector.

In addition, the process herein can be used for in vitro mutagenesis. The oligonucleotide primers need not be exactly complementary to the nucleic acid sequence which is being amplified. It is only necessary that they be able to hybridize to the sequence sufficiently well to be extended by the thermostable enzyme. The product of an amplification reaction wherein the primers employed are not exactly complementary to the original template will contain the sequence of the primer rather than the template, thereby introducing an in vitro mutation. In further cycles this mutation will be amplified with an undiminished efficiency because no further mispaired primings are required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers to induce further sequence changes. In this way a series of mutated sequences could gradually be produced wherein each new addition to the series could differ from the last in a minor way, but from the original DNA source sequence in an increasingly major way. In this manner changes could be made ultimately which were not feasible in a single step due to the inability of a very seriously mismatched primer to function.

In addition, the primer can contain as part of its sequence a non-complementary sequence, provided that a sufficient amount of the primer contains a sequence which is complementary to the strand to be amplified. For example, a nucleotide sequence which is not complementary to the template sequence (such as, e.g., a promoter, linker, coding sequence, etc.) may be attached at the 5' end of one or both of the primers, and thereby appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

The method herein may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed but where rapid detection is desirable.

For purposes of this invention genetic diseases may include specific deletions and/or mutations in genomic DNA from any organism, such as, e.g., sickle cell anemia, α-thalassemia, β-thalassemia, and the like. Sickle cell anemia can be readily detected via oligomer restriction analysis as described in EP Patent Publication 164,054 published Dec. 11, 1985, or via a RFLP-like analysis following amplification of the appropriate DNA sequence by the present method. α-Thalassemia can be detected by the absence of a sequence, and β-thalassemia can be detected by the presence of a polymorphic restriction site closely linked to a mutation that causes the disease.

All of these genetic diseases may be detected by amplifying the appropriate sequence and analyzing it by Southern blots without using radioactive probes. In such a process, for example, a small sample of DNA from, e.g., amniotic fluid containing a very low level of the desired sequence is amplified, cut with a restriction enzyme, and analyzed via a Southern blotting technique. The use of non-radioactive probes is facilitated by the high level of the amplified signal.

In another embodiment, a small sample of DNA may be amplified to a convenient level and then a further cycle of extension reactions performed wherein nucleotide derivatives which are readily detectable (such as $^{32}$P-labeled or biotin-labeled nucleotide triphosphates) are incorporated directly into the final DNA product, which may be analyzed by restriction and electrophoretic separation or any other appropriate method.

In a further embodiment, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

A practical application of this technique can be illustrated by its use in facilitating the detection of sickle cell anemia via the oligomer restriction technique described herein and in EP 164,054, supra, and Saiki et al., Bio/Technology, 3, pp 1008–1012 (1985), the disclosures of which are incorporated herein by reference. Sickle cell anemia is a hemoglobin disease which is caused by a single base pair change in the sixth codon of the α-globin gene.

The method of this invention may also be used to detect directly single-base pair variations in nucleic acid sequence (such as genomic DNA) using sequence-specific oligonucleotides. This particular method is described in U.S. Ser. No. 899,344 filed Aug. 22, 1986, now abandoned in favor of continuation application U.S. Ser. No. 07/491,210, filed Mar. 9, 1990 the disclosure of which is incorporated herein by reference.

In this method, the sequence variation, whether resulting from cancer, an infectious disease, or a genetic disease, e.g., a genetic lesion, is directly detected, eliminating the need for restriction digestion, electrophoresis, and gel manipulations otherwise required. The use of sequence-specific oligonucleotides in a dot blot format after amplification, as described herein, provides for improved specificity and sensitivity of the probe; an interpretable signal can be obtained with a 0.04 µg sample in six hours. Also, if the amount of sample spotted on a membrane is increased to 0.1–0.5 µg, non-isotopically labeled oligonucleotides may be utilized rather than the radioactive probes used in previous methods. Furthermore, the process described hereinbelow is applicable to use of sequence-specific oligonucleotides less than 19-mers in size, thus allowing use of more discriminatory sequence-specific oligonucleotides.

Regarding genetic diseases, while RFLP requires a polymorphic restriction site to be associated with the disease, sequence-specific oligonucleotides directly detect the genetic lesion and are generally more useful for the analysis of such diseases as hemoglobin C disease, α-1-antitrypsin and β-thalassemia, which result from single-base mutations. In addition, the oligonucleotides can be used to distinguish between genetic variants which represent different alleles (e.g., HLA typing), indicating the feasibility of a sequence-specific oligonucleotide-based HLA typing kit that includes a thermostable enzyme.

In one embodiment of the invention herein wherein a nucleotide variation in sequence is to be detected, the sample, amplified as described above using one primer for each strand of each nucleic acid suspected of containing the nucleotide variation, is spotted directly on a series of membranes and each membrane is hybridized with a different labeled sequence-specific oligonucleotide probe. One procedure for spotting the sample on a membrane is descibed by Kafotos et al., *Nucleic Acids Research*, 7:1541–1552 (1979), the disclosure of which is incorporated herein by reference.

Briefly, the DNA sample affixed to the membrane may be pretreated with a prehybridization solution containing sodium dodecyl sulfate, Ficoll, serum albumin and various salts prior to the probe being added. Then, a labeled oligonucleotide probe which is specific to each sequence variation to be detected is added to a hybridization solution similar to the prehybridization solution. The hybridization solution is applied to the membrane and the membrane is subjected to hybridization conditions that will depend on the probe type and length, the type and concentration of ingredients, etc. Generally, hybridization is carried out at about 25 to 75° C., preferably 35 to 65° C., for 0.25–50 hours, preferably less than three hours. The greater the stringency of conditions, the greater the required complementarity for hybridization between the probe and sample. If the background level is high, stringency may be increased accordingly. The stringent conditions can also be incorporated in the wash.

After the hybridization, the sample is washed of unhybridized probe using any suitable means such as by washing one or more times with varying concentrations of standard saline phosphate EDTA (SSPE) (180 mM NaCl, 10 mM NaHPO$_4$ and 1 M EDTA, pH 7.4) solutions at 25–75° C. for about 10 minutes to one hour, depending on the temperature. The label is then detected by using any appropriate detection technique.

The sequence-specific oligonucleotide employed herein is an oligonucleotide which is generally prepared and selected as described above for preparing and selecting the primers. As described above, the sequence-specific oligonucleotide must encompass the region of the sequence which spans the nucleotide variation being detected and must be specific for the nucleotide variation being detected. For example, if it is desired to detect whether a sample contains the mutation for sickle cell anemia, one oligonucleotide will be prepared which contains the nucleotide sequence site characteristic of the normal β-globin gene and one oligonucleotide will be prepared which contains the nucleotide sequence characteristic of the sickle cell allele. Each oligonucleotide would be hybridized to duplicates of the same sample to determine whether the sample contains the mutation.

The polymorphic areas of HLA class II genes are localized to specific regions of the first exon and are flanked by conserved sequences, so that oligonucleotide primers complementary to opposite strands of the conserved 5' and 3' ends of the first exon can be prepared.

The number of oligonucleotides employed for detection of the polymorphic areas of the HLA class II genes will vary depending on the type of gene, which has regions of base pair variation which may be clustered or spread apart. If the regions are clustered, as in the case with HLA-DQ-α, then one oligonucleotide is employed for each allele. If the regions are spread apart, as in the case with HLA-DQ-β and HLA-DR-β, then more than one probe, each encompassing an allelic variant, will be used for each allele. In the case of HLA-DQ-β and HLA-DR-β, three probes are employed for the three regions of the locus where allelic variations may occur. For detection of insulin-dependent diabetes mellitus (IDDM) four probes for the HLA-DRβ second exon are employed.

Haplotypes can be inferred from segregation analysis in families or, in some cases, by direct analysis of the individual DNA sample. Specific allelic combinations (haplotypes) of sequence-specific oligonucleotide reactivities can be identified in heterozygous cells by using restriction enzyme digestion of the genomic DNA prior to amplification.

For example, if in DQβ one finds three highly variable subregions A, B, and C within a single amplified region, and if there are six different sequences at each region (A, sequences 1–6, B, sequence 1–6, C, sequence 1–6) then an individual could be typed in the DQβ locus by sequence-specific oligonucleotide probe analysis as containing A1, A2; B2, B3; C1, C4, with the possible haplotype combinations of A1, B2, C1; A1, B2, C4; A2, B2, C1; A2, B2, C4; A1, B3, C1; A1, B3, C4; A1, B2, C1; and A1, B2, C4.

If the genomic DNA is digested with a polymorphic restriction enzyme prior to amplification, and if the enzyme cuts both alleles between the primers, there is no reactivity with the sequence-specific probes due to lack of amplification, and the result is uninformative. If the enzyme cuts neither allele, the probe results with digested and undigested genomic DNA are the same and the result is uninformative. If the enzyme cuts only one allele, however, then one can infer both haplotypes by comparing the probe reactivity patterns on digested and undigested DNA.

The haplotypes can be deduced by comparing sequence-specific oligonucleotide reactivities with uncut genomic DNA and genomic DNA cut with one or several enzymes known to be polymorphic and to recognize sites between the primers.

The length of the sequence-specific oligonucleotide will depend on many factors, including the particular target molecule being detected, the source of oligonucleotide, and the nucleotide composition. For purposes herein, the sequence-specific oligonucleotide typically contains 15–25 nucleotides, although it may contain more or fewer nucleotides. While oligonucleotides which are at least 19 mers in length may enhance specificity and/or sensitivity, probes which are less than 19 mers, e.g., 16-mers, may show more sequence-specific discrimination presumably because a single mismatch is more destabilizing. Because amplification increases specificity so that a longer length is less critical, and hybridization and washing temperatures can be lower for the same salt concentration, it is preferred to use oligonucleotides which are less than 19 mers in length.

Where the sample is first placed on the membrane and then detected with the oligonucleotide, the oligonucleotide must be labeled with a suitable label moiety, which may be detected by spectroscopic, photochemical, biochemical, immunochemical or chemical means. Immunochemical means include antibodies which are capable of forming a complex with the oligonucleotide under suitable conditions, and biochemical means include polypeptides or lectins capable of forming a complex with the oligonucleotide under the appropriate conditions. Examples include fluorescent dyes, electron-dense reagents, enzymes capable of depositing insoluble reaction products or being detected chromogenically, such as horseradish peroxidase, alkaline phosphatase, a radioactive label such as $^{32}P$, or biotin. If biotin is employed, a spacer arm may be utilized to attach it to the oligonucleotide. Preferably, the label moiety is horseradish peroxidase.

Alternatively, in one "reverse" dot blot format, at least one of the primers and/or at least one of the four nucleotide triphosphates is labeled with a detectable label, so that the resulting amplified sequence is labeled. These labeled moieties may be present initially in the reaction mixture or added during a later cycle of the amplification to introduce the label to the amplification product. Then an unlabeled sequence-specific oligonucleotide capable of hybridizing with the amplified nucleic acid sequence, if the sequence variation(s) (whether normal or mutant) is/are present, is spotted on (affixed to) the membrane under prehybridization conditions as described above. The amplified sample is then added to the pretreated membrane under hybridization conditions as described above. Finally, detection means are used to determine if an amplified sequence in the nucleic acid sample has hybridized to the oligonucleotide affixed to the membrane. Hybridization will occur only if the membrane-bound sequence containing the variation is present in the amplification product, i.e., only if a sequence of the probe is complementary to a region of the amplified sequence.

In another version of the "reverse" dot blot format, the amplification is carried out without employing a label as with the "forward" dot blot format described above, and a labeled sequence-specific oligonucleotide probe capable of hybridizing with the amplified nucleic acid sequence containing the variation, if present, is spotted on (affixed to) the membrane under prehybridization conditions as described above. The amplified sample is then added to the pretreated membrane under hybridization conditions as described above. Then the labeled oligonucleotide or a fragment thereof is released from the membrane in such a way that a detection means can be used to determine if an amplified sequence in the sample hybridized to the labeled oligonucleotide. The release may take place, for example, by adding a restriction enzyme to the membrane which recognizes a restriction site in the probe. This procedure, known as oligomer restriction, is described more fully in EP Patent Publication 164,054 published Dec. 11, 1985, the disclosure of which is incorporated herein by reference.

In both the forward and reverse dot blot methods, the genetic diseases which may be detected include specific deletions, insertions and/or substitutions in any base pair mutation or polymorphism in nucleic acids, for example, genomic DNA, from any organism. Examples of diseases in which base pair variation is known include sickle cell anemia, hemoglobin C disease, α-thalassemia, β-thalassemia, and the like. Other diseases that may be detected include cancerous diseases such as those involving the RAS oncogenes, e.g., the n-RAS oncogene, and infectious diseases.

A dot blot process may also be used for HLA typing in the areas of tissue transplantation, disease susceptibility, and paternity determination. The HLA class II genes, consisting of the α and β genes from the HLA-DR, HLA-DQ and HLA-DP regions, are highly polymorphic; their genetic complexity at the DNA level is significantly greater than the polymorphism currently defined by serological typing. In addition, the process herein may be employed to detect certain DNA sequences coding for HLA class II β proteins (IDDM) as described more fully in copending U.S. Ser. No 899,512 filed Aug. 22, 1986, the disclosure of which is incorporated herein by reference. Briefly, the four DNA sequences associated with IDDM are selected from the group consisting of:

| | |
|---|---:|
| 5'-GAGCTGCGTAAGTCTGAG-3', | 1) |
| 5'-GAGGAGTTCCTGCGCTTC-3', | 2) |
| 5'-CCTGTCGCCGAGTCCTGG-3', | 3) | and

| | |
|---|---:|
| 5'-GACATCCTGGAAGACGAGAGA-3', | 4) | or the DNA strands that are complementary thereto. Sequence-specific probes may be prepared that will hybridize to one or more of these sequences.

Various infectious diseases can be diagnosed by the presence in clinical samples of specific DNA sequences characteristic of the causative microorganism. These include bacteria, such as Salmonella, Chlamydia, Neisseria; viruses, such as the hepatitis viruses, and parasites, such as the Plasmodium responsible for malaria. U.S. Patent Reexamination Certificate B14,358,535 issued on May 13, 1986 to Falkow et al. describes the use of specific DNA hybridization probes for the diagnosis of infectious diseases. A relatively small number of pathogenic organisms may be present in a clinical sample from an infected patient and the DNA extracted from these may constitute only a very small fraction of the total DNA in the sample. Specific amplification of suspected sequences prior to immobilization and hybridization detection of the DNA samples could greatly improve the sensitivity and specificity of traditional procedures.

Routine clinical use of DNA probes for the diagnosis of infectious diseases would be simplified considerably if non-radioactively labeled probes could be employed as described in EP 63,879 to Ward. In this procedure biotin-containing DNA probes are detected by chromogenic enzymes linked to avidin or biotin-specific antibodies. This type of detection is convenient, but relatively insensitive. The combination of specific DNA amplification by the present method and the use of stably labeled probes could provide the convenience and sensitivity required to make the Falkow and Ward procedures useful in a routine clinical setting.

A specific use of the amplification technology for detecting or monitoring for the AIDS virus is described in U.S. Ser. No. 818,127 filed Jan. 10, 1986, now abandoned the disclosure of which is incorporated herein by reference. Briefly, the amplification and detection process is used with primers and probes which are designed to amplify and detect, respectively, nucleic acid sequences which are substantially conserved among the nucleic acids in AIDS viruses and specific to the nucleic acids in AIDS viruses. Thus, the sequence to be detected must be sufficiently complementary to the nucleic acids in AIDS viruses to initiate polymerization, preferably at room temperature, in the presence of the enzyme and nucleotide triphosphates.

In addition, the probe may be a biotinylated probe in which the biotin is attached to a spacer arm of the formula:

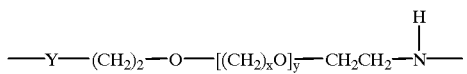

where Y is O, NH or N—CHO, x is a number from 1 to 4, and y is a number from 2 to 4. The spacer arm is in turn attached to a psoralen moiety of the formula:

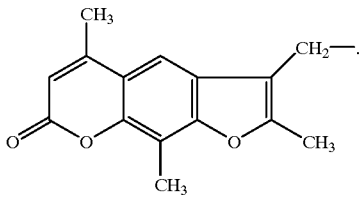

The psoralen moiety intercalates into and crosslinks a "gapped circle" probe as described by Courage-Tebbe et al., Biochim. Biophys. Acta, 697 (1982) 1–5, wherein the single-stranded hybridization region of the gapped circle spans the region contained in the primers. The details of this biotinylation and dot blot procedure are described more fully in commonly assigned U.S. Pat. No. 4,582,789 issued Apr. 15, 1986 and U.S. Pat. No. 4,617,261 issued Oct. 14, 1986, the disclosures of which are incorporated herein by reference.

The amplification process can also be utilized to produce sufficient quantities of DNA from a single copy human gene such that detection by a simple non-specific DNA stain such as ethidium bromide can be employed to diagnose DNA directly.

In addition to detecting infectious diseases and pathological abnormalities in the genome of organisms, the process herein can also be used to detect DNA polymorphism that may not be associated with any pathological state.

The following examples are offered by way of illustration and are not intended to limit the invention in any manner. In these examples all percentages are by weight if for solids and by volume if for liquids, unless otherwise noted, and all temperatures are in degrees Celsius unless otherwise noted.

EXAMPLE I

I. Synthesis of the Primers

The following two oligonucleotide primers were prepared by the method described below:

```
5'-ACACAACTGTGTTCACTAGC-3'        (PC03)

5'-CAACTTCATCCACGTTCACC-3'        (PC04)
```

These primers, both 20-mers, anneal to opposite strands of the genomic DNA with their 5' ends separated by a distance of 110 base pairs.

A. Automated Synthesis Procedures

The diethylphosphoramidites, synthesized according to Beaucage and Caruthers (Tetrahedron Letters (1981) 22:1859–1862) were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

B. Oligodeoxyribonucleotide Deprotection and Purification Procedures

The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

C. Characterization of Oligodeoxyribonucleotides

Test aliquots of the purified oligonucleotides were $^{32}P$ labeled with polynucleotide kinase and $\gamma\text{-}^{32}P\text{-ATP}$. The labeled compounds were examined by autoradiography of 14–20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Isolation of Human Genomic DNA from Cell Line

High molecular weight genomic DNA was isolated from a T cell line, Molt 4, homozygous for normal β-globin available from the Human Genetic Mutant Cell Depository, Camden, N.J. as GM2219C using essentially the method of Maniatis et al., supra, p. 280–281.

III. Purification of a Polymerase From Thermus aguaticus

Thermus aquaticus strain YT1, available without restriction from the American Type Culture Collection, 12301 Parklawn Drive, Rockville, Md., as ATCC No. 25,104 was grown in flasks in the following medium:

| | |
|---|---|
| Sodium Citrate | 1 mM |
| Potassium Phosphate, pH 7.9 | 5 mM |
| Ammonium Chloride | 10 mM |
| Magnesiurn Sulfate | 0.2 mM |
| Calcium Chloride | 0.1 mM |
| Sodium Chloride | 1 g/l |
| Yeast Extract | 1 g/l |
| Tryptone | 1 g/l |
| Glucose | 2 g/l |
| Ferrous Sulfate | 0.01 mM |

(The pH was adjusted to 8.0 prior to autoclaving.)

A 10-liter fermentor was inoculated from a seed flask cultured overnight in the above medium at 70° C. A total of 600 ml from the seed flask was used to inoculate 10 liters of the same medium. The pH was controlled at 8.0 with ammonium hydroxide with the dissolved oxygen at 40%, with the temperature at 70° C., and with the stirring rate at 400 rpm.

After growth of the cells, they were purified using the protocol (with slight modification) of Kaledin et al., supra, through the first five stages and using a different protocol for the sixth stage. All six steps were conducted at 4° C. The rate of fractionation on columns was 0.5 columns/hour and the volumes of gradients during elution were 10 column volumes. An alternative and preferred purification protocol is described in U.S. Ser. No. 07/063,509 filed Jun. 17, 1987 which issued as U.S. Pat. No. 4,889,818 to Gelfand et al., entitled "Purified Thermostable Enzyme", the entire disclosure of which is incorporated herein by reference.

Briefly, the above culture of the *T. aquaticus* cells was harvested by centrifugation after nine hours of cultivation, in late log phase, at a cell density of 1.4 g dry weight/l. Twenty grams of cells were resuspended in 80 ml of a buffer consisting of 50 mM Tris.HCl pH 7.5, 0.1 mM EDTA. Cells were lysed and the lysate was centrifuged for two hours at 35,000 rpm in a Beckman TI 45 rotor at 4° C. The supernatant was collected (fraction A) and the protein fraction precipitating between 45 and 75% saturation of ammonium sulfate was collected, dissolved in a buffer consisting of 0.2 M potassium phosphate buffer, pH 6.5, 10 mM 2-mercaptoethanol, and 5% glycerine, and finally dialyzed against the same buffer to yield fraction B.

Fraction B was applied to a 2.2×33-cm column of DEAE-cellulose, equilibrated with the above described buffer. The column was then washed with the same buffer and the fractions containing protein (determined by absorbance at 280 nm) were collected. The combined protein fraction was dialyzed against a second buffer, containing 0.01 M potassium phosphate buffer, pH 7.5, 10 mM 2-mercaptoethanol, and 5% glycerine, to yield fraction C.

Fraction C was applied to a 2.6×21-cm column of hydroxyapatite, equilibrated with a second buffer. The column was then washed and the enzyme was eluted with a linear gradient of 0.01–0.5 M potassium phosphate buffer, pH 7.5, containing 10 mM 2-mercaptoethanol and 5% glycerine. Fractions containing DNA polymerase activity (90–180 mM potassium phosphate) were combined, concentrated four-fold using an Amicon stirred cell and YM10 membrane, and dialyzed against the second buffer to yield fraction D.

Fraction D was applied to a 1.6×28-cm column of DEAE-cellulose, equilibrated with the second buffer. The column was washed and the polymerase was eluted with a linear gradient of 0.01–0.5 M potassium phosphate in the second buffer. The fractions were assayed for contaminating endonuclease(s) and exonuclease(s) by electrophoretically detecting the change in molecular weight of phage λ DNA or supercoiled plasmid DNA after incubation with an excess of DNA polymerase (for endonuclease) and after treatment with a restriction enzyme that cleaves the DNA into several fragments (for exonuclease). Only those DNA polymerase fractions (65–95 mM potassium phosphate) having minimal nuclease contamination were pooled. To the pool was added autoclaved gelatin in an amount of 250 μg/ml, and dialysis was conducted against the second buffer to yield Fraction E.

Fraction E was applied to a phosphocellulose column and eluted with a 100 ml gradient (0.01–0.4 M KCl gradient in 20 mM potassium phosphate buffer pH 7.5). The fractions were assayed for contaminating endo/exonuclease(s) as described above as well as for polymerase activity (by the method of Kaledin et al.) and then pooled. The pooled fractions were dialyzed against the second buffer, then concentrated by dialysis against 50% glycerine and the second buffer.

The molecular weight of the polymerase was determined by SDS PAGE. Marker proteins (Bio-Rad low molecular weight standards) were phosphorylase B (92,500), bovine serum albumin (66,200), ovalbumin (45,000), carbonic anhydrase (31,000), soybean trypsin inhibitor (21,500), and lysozyme (14,400).

Preliminary data suggest that the polymerase has a molecular weight of about 86,000–90,000 daltons, not 62,000–63,000 daltons reported in the literature (e.g., by Kaledin et al.).

The polymerase was incubated in 50 μl of a mixture containing 25 mM Tris-HCl pH 6.4 and pH 8.0, 0.1 M KCl, 10 mM MgCl$_2$, 1 mM 2-mercaptoethanol, 10 nmoles each of dGTP, dATP, and TTP, and 0.5 μCi ($^3$H) dCTP, 8 μg "activated" calf thymus DNA, and 0.5–5 units of the polymerase. "Activated" DNA is a native preparation of DNA after partial hydrolysis with DNase I until 5% of the DNA was transferred to the acid-soluble fraction. The reaction was conducted at 70° C. for 30 minutes, and stopped by adding 50 μl of a saturated aqueous solution of sodium pyrophosphate containing 0.125 M EDTA-Na$_2$. Samples were processed and activity was determined as described by Kaledin et al., supra.

The results showed that at pH 6.4 the polymerase was more than one-half as active as at pH 8.0. In contrast, Kaledin et al. found that at pH about 7.0, the enzyme therein had 8% of the activity at pH 8.3. Therefore, the pH profile for the instant thermostable enzyme is broader than that for the Kaledin et al. enzyme.

Finally, when only one or more nucleotide triphosphates were eliminated from a DNA polymerase assay reaction mixture, very little, if any, activity was observed using the enzyme herein, which activity was consistent with the expected value and with an enzyme exhibiting high fidelity. In contrast, the activity obtained using the Kaledin et al. (supra) enzyme is not consistent with the expected value, and suggests misincorporation of nucleotide triphosphate(s).

IV. Amplification Reaction

One microgram of the genomic DNA described above was diluted in an initial 100 μl aqueous reaction volume containing 25 mM Tris.HCl buffer (pH 8.0), 50 mM KCl, 10 mM MgCl$_2$, 5 mM dithiothreitol, 200 μg/ml gelatin, 1 μM of primer PC03, 1 μM of primer PC04, 1.5 mM dATP, 1.5 mM dCTP, 1.5 mM dGTP and 1.5 mM TTP. The sample was heated for 10 minutes at 98° C. to denature the genomic DNA, then cooled to room temperature. Four microliters of the polymerase from *Thermus aquaticus* was added to the reaction mixture and overlaid with a 100 μl mineral oil cap. The sample was then placed in the aluminum heating block of the liquid handling and heating instrument described in U.S. application Ser. No. 833,368 filed Feb. 25, 1986, now abandoned the disclosure of which is incorporated herein by reference.

The DNA sample underwent 20 cycles of amplification in the machine, repeating the following program cycle:

1) heating from 37° C. to 98° C. in heating block over a period of 2.5 minutes; and
2) cooling from 98° C. to 37° C. over a period of three minutes to allow the primers and DNA to anneal.

After the last cycle, the sample was incubated for an additional 10 minutes at 55° C. to complete the final extension reaction.

V. Synthesis and Phosphorylation of Oligodeoxyribonucleotide Probes

A labeled DNA probe, designated RS24, of the following sequence was prepared:

5'-*CCCACAGGGCAGTAACGGCAGACTTCTC-
    CTCAGGAGTCAG-3'    (RS24)

where * indicates the label. This probe is 40 bases long, spans the fourth through seventeenth codons of the gene, and is complementary to the normal β-globin allele ($\beta^A$). The schematic diagram of primers and probes is given below:

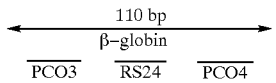

This probe was synthesized according to the procedures described in Section I of Example I. The probe was labeled by contacting 20 pmole thereof with 4 units of T4 polynucleotide kinase (New England Biolabs) and about 40 pmole γ-$^{32}$P-ATP (New England Nuclear, about 7000 Ci/mmole) in a 40 μl reaction volume containing 70 mM Tris buffer (pH 7.6), 10 mM MgCl$_2$, 1.5 mM spermine, and 10 mM dithiothreitol for 60 minutes at 37° C. The total volume was then adjusted to 100 μl with 25 mM EDTA and purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris buffer, 0.1 mM EDTA, pH 8.0). TCA precipitation of the reaction product indicated that for RS24 the specific activity was 4.3 μCi/pmole and the final concentration was 0.118 pmole/μl.

VI. Dot Blot Hybridizations

Four microliters of the amplified sample from Section IV and 5.6 μl of appropriate dilutions of β-globin plasmid DNA calculated to represent amplification efficiencies of 70, 75, 80, 85, 90, 95 and 100% were diluted with 200 μl 0.4 N NaOH, 25 mM EDTA and spotted onto a Genatran 45 (Plasco) nylon filter by first wetting the filter with water, placing it in a Bio-Dot (Bio-Rad, Richmond, Calif.) apparatus for preparing dot blots which holds the filters in place, applying the samples, and rinsing each well with 0.1 ml of 20×SSPE (3.6 M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20×SSPE, and baked for 30 minutes at 80° C. in a vacuum oven.

After baking, each filter was then contacted with 16 ml of a hybridization solution consisting of 3×SSPE, 5×Denhardt's solution (1×=0.02% polyvinylpyrrolidone, 0.02% Ficoll, 0.02% bovine serum albumin, 0.2 mM Tris, 0.2 mM EDTA, pH 8.0), 0.5% SDS and 30% formamide, and incubated for two hours at 42° C. Then 2 pmole of probe RS24 was added to the hybridization solution and the filter was incubated for two minutes at 42° C.

Finally, each hybridized filter was washed twice with 100 ml of 2×SSPE and 0.1% SDS for 10 minutes at room temperature. Then the filters were treated once with 100 ml of 2×SSPE, 0.1% SDS at 60° C. for 10 minutes.

Each filter was then autoradiographed, with the signal readily apparent after two hours.

VII. Discussion of Autoradiogram

The autoradiogram of the dot blots was analyzed after two hours and compared in intensity to standard serial dilution β-globin reconstructions prepared with HaeIII/MaeI-digested pBR:$\beta^A$, where $\beta^A$ is the wild-type allele, as described in Saiki et al *Science*, supra. Analysis of the reaction product indicated that the overall amplification efficiency was about 95%, corresponding to a 630,000–fold increase in the β-globin target sequence.

EXAMPLE II

I. Amplification Reaction

Two 1 μg samples of genomic DNA extracted from the Molt 4 cell line as described in Example I were each diluted in a 100 μl reaction volume containing 50 mM KCl, 25 mM Tris.HCl buffer pH 8.0, 10 mM MgCl$_2$, 1 μM of primer PC03, 1 μM of primer PC04, 200 μg/ml gelatin, 10% dimethylsulfoxide (by volume), and 1.5 mM each of dATP, dCTP, dGTP and TTP. After this mixture was heated for 10 minutes at 98° C. to denature the genomic DNA, the samples were cooled to room temperature and 4 μl of the polymerase from *Thermus aquaticus* described in Example I was added to each sample. The samples were overlaid with mineral oil to prevent condensation and evaporative loss.

One of the samples was placed in the heating block of the machine described in Example I and subjected to 25 cycles of amplification, repeating the following program cycle:

(1) heating from 37 to 93° C. over a period of 2.5 minutes;
(2) cooling from 93° C. to 37° C. over a period of three minutes to allow the primers and DNA to anneal; and
(3) maintaining at 37° C. for two minutes.

After the last cycle the sample was incubated for an additional 10 minutes at 60° C. to complete the final extension reaction.

The second sample was placed in the heat-conducting container of the machine, described in more detail in U.S. Ser. No. 899,061 filed Aug. 22, 1986 now abandoned in favor of divisional application U.S. Ser. No. 07/494,174, filed Mar. 14, 1990, which issued as U.S. Pat. No. 5,038,852. The heat-conducting container is attached to Peltier heat pumps which adjust the temperature upwards or downwards and a microprocessor controller to control automatically the amplification sequence, the temperature levels, the temperature ramping and the timing of the temperature.

The second sample was subjected to 25 cycles of amplification, repeating the following program cycle:

(1) heating from 37 to 95° C. over a period of three minutes;
(2) maintaining at 95° C. for 0.5 minutes to allow denaturation to occur;
(3) cooling from 95 to 37° C. over a period of one minute; and
(4) maintaining at 37° C. for one minute.

II. Analysis

Two tests were done for analysis, a dot blot and an agarose gel analysis.

For the dot blot analysis, a labeled DNA probe, designated RS18, of the following sequence was prepared.

5'-*CTCCTGAGGAGAAGTCTGC-3'    (RS18)

where * indicates the label. This probe is 19 bases long, spans the fourth through seventeenth codons of the gene, and is complementary to the normal β-globin allele ($\beta^A$). The schematic diagram of primers and probes is given below:

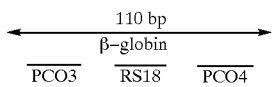

This probe was synthesized according to the procedures described in Section I of Example I. The probe was labeled by contacting 10 pmole thereof with 4 units of T4 polynucleotide kinase (New England Biolabs) and about 40 pmole $\gamma$-$^{32}$P-ATP (New England Nuclear, about 7000 Ci/mmole) in a 40 $\mu$l reaction volume containing 70 mM Tris.HCl buffer (pH 7.6), 10 mM $MgCl_2$, 1.5 mM spermine and 10 mM dithiothreitol for 60 minutes at 37° C. The total volume was then adjusted to 100 $\mu$l with 25 mM EDTA and purified according to the procedure of Maniatis et al., supra, p. 466–467 over a 1 ml Bio Gel P-4 (BioRad) spin dialysis column equilibrated with Tris-EDTA (TE) buffer (10 mM Tris.HCl buffer, 0.1 mM EDTA, pH 8.0). TCA precipitation of the reaction product indicated that for RS18 the specific activity was 4.6 $\mu$Ci/pmole and the final concentration was 0.114 pmole/$\mu$l.

Five microliters of the amplified sample from Section I and of a sample amplified as described above except using the Klenow fragment of *E. coli* DNA Polymerase I instead of the thermostable enzyme were diluted with 195 $\mu$l 0.4 N NaOH, 25 mM EDTA and spotted onto two replicate Genatran 45 (Plasco) nylon filters by first wetting the filters with water, placing them in a Bio-Dot (Bio-Rad, Richmond, Calif.) apparatus for preparing dot blots which holds the filters in place, applying the samples, and rinsing each well with 0.4 ml of 20×SSPE (3.6 M NaCl, 200 mM $NaH_2PO_4$, 20 MM EDTA), as disclosed by Reed and Mann, supra. The filters were then removed, rinsed in 20×SSPE, and baked for 30 minutes at 80° C. in a vacuum oven.

After baking, each filter was then contacted with 6 ml of a hybridization solution consisting of 5×SSPE, 5×Denhardt's solution (1×=0.02% polyvinylpyrrolidone, 0.02% Ficoll, 0.02% bovine serum albumin, 0.2 mM Tris, 0.2 mM EDTA, pH 8.0) and 0.5% SDS, and incubated for 60 minutes at 55° C. Then 5 $\mu$l of probe RS18 was added to the hybridization solution and the filter was incubated for 60 minutes at 55° C.

Finally, each hybridized filter was washed twice with 100 ml of 2×SSPE and 0.1% SDS for 10 minutes at room temperature. Then the filters were treated twice more with 100 ml of 5×SSPE, 0.1% SDS at 60° C. for 1) one minute and 2) three minutes, respectively.

Each filter was then autoradiographed, with the signal readily apparent after 90 minutes.

In the agarose gel analysis, 5 $\mu$l each amplification reaction was loaded onto 4% NuSieve/0.5% agarose gel in 1×TBE buffer (0.089 M Tris, 0.089 M boric acid, and 2 mM EDTA) and electrophoresed for 60 minutes at 100V. After staining with ethidium bromide, DNA was visualized by UV fluorescence.

The results show that the machines used in Example I and this example were equally effective in amplifying the DNA, showing discrete high-intensity 110-base pair bands of similar intensity, corresponding to the desired sequence, as well as a few other discrete bands of much lower intensity. In contrast, the amplification method as described in Example I of copending U.S. application Ser. No. 839,331 filed Mar. 13, 1986, supra, which involves reagent transfer after each cycle using the Klenow fragment of *E. coli* Polymerase I, gave a DNA smear resulting from the non-specific amplification of many unrelated DNA sequences.

It is expected that similar improvements in amplification and detection would be achieved in evaluating HLA-DQ, DR and DP regions.

If in the above experiments the amplification reaction buffer contains 2 mM $MgCl_2$ instead of 10 mM $MgCl_2$ and 150–200, $\mu$M of each nucleotide rather than 1.5 mM of each, and if the lower temperature of 37° C. is raised to 45–58° C. during amplification, better specificity and efficiency of amplification occurs. Also, DMSO was found not necessary or preferred for amplification.

EXAMPLE III

Amplification and Cloning

For amplification of a 119-base pair fragment on the human $\beta$-globin gene, a total of 1 microgram each of human genomic DNA isolated from the Molt 4 cell line or from the GM2064 cell line (representing a homozygous deletion of the $\beta$- and $\delta$-hemoglobin region and available from the Human Genetic Mutant Cell Depository, Camden, N.J.) as described above was amplified in a 100 $\mu$l reaction volume containing 50 mM KCl, 25 mM Tris.HCl pH 8, 10 mM $MgCl_2$, 200 $\mu$g/ml gelatin, 5 mM 2-mercaptoethanol, 1.5 mM each of dATP, dCTP, TTP, and dGTP, and 1 $\mu$M of each of the following primers:

| | |
|---|---|
| 5'-CTTCTGcagCAACTGTGTTCACTAGC-3' | (GH18) |
| 5'-CACaAgCTTCATCCACGTTCACC-3' | (GH19) | where lower case letters denote mismatches from wild-type sequence to create restriction enzyme sites. GH18 is a 26-base-oligonucleotide complementary to the negative strand and contains an internal PstI site. GH19 is a 29-base oligonucleotide complementary to the plus strand and contains an internal HindIII recognition sequence. These primers were selected by first screening the regions of the gene for homology to the PstI and HindIII restriction sites. The primers were then prepared as described in Example I.

The above reaction mixtures were heated for 10 minutes at 95° C. and then cooled to room temperature. A total of 4 $\mu$l of the polymerase described in Example I was added to each reaction mixture, and then each mixture was overlayed with mineral oil. The reaction mixtures were subjected to 30 cycles of amplification with the following program:

2.5 min. ramp, 37 to 98° C.

3 min. ramp, 98 to 37° C.

2 min. soak, 37° C.

After the last cycle, the reaction mixtures were incubated for 20 minutes at 65° C. to complete the final extension. The mineral oil was extracted with chloroform and the mixtures were stored at −20° C.

A total of 10 $\mu$l of the amplified product was digested with 0.5 $\mu$g M13mp10 cloning vector, which is publicly available from Boehringer-Mannheim, in a 50 $\mu$l volume containing 50 mM NaCl, 10 mM Tris.HCl, pH 7.8, 10 mM $MgCl_2$, 20 units PstI and 26 units HindIII for 90 minutes at 37° C. The reaction was stopped by freezing at −20° C. The volume was adjusted to 110 $\mu$l with TE buffer and loaded (100 $\mu$l) onto a 1 ml BioGel P-4 spin dialysis column. One 0.1 ml fraction was collected and ethanol precipitated.

(At this point it was discovered that there was $\beta$-globin amplification product in the GM2064 sample. Subsequent experiments traced the source of contamination to the primers, either GH18 or GH19. Because no other source of primers was available, the experiment was continued with the understanding that some cloned sequences would be derived from the contaminating DNA in the primers.)

The ethanol pellet was resuspended in 15 $\mu$l water, then adjusted to 20 $\mu$l volume containing 50 mM Tris.HCl, pH 7.8, 10 mM $MgCl_2$, 0.5 mM ATP, 10 mM dithiothreitol, and 400 units ligase. [One unit is the amount of enzyme required to give 50% ligation of HindIII digested λDNA in 30 minutes at 16° C. in 20 μl at a 5' termini concentration of 0.12 mM (about 330 μg/ml)]. This mixture was incubated for three hours at 16° C.

Ten microliters of ligation reaction mixture containing Molt 4 DNA was transformed into *E. coli* strain JM103 competent cells, which are publicly available from BRL in Bethesda, Md. The procedure followed for preparing the transformed strain is described in Messing, J. (1981) *Third Cleveland Symposium on Macromolecules:Recombinant DNA*, ed. A. Walton, Elsevier, Amsterdam, 143–163. A total of 651 colorless plaques (and 0 blue plaques) were obtained. Of these, 119 had a (+)-strand insert (18%) and 19 had a (−)-strand insert (3%). This is an increase of almost 20-fold over the percentage of β-globin positive plaques among the primer-positive plaques from the amplification technique using Klenow fragment of *E. coli* Polymerase I, where the reaction proceeded for two minutes at 25° C., after which the steps of heating to 100° C. for two minutes, cooling, adding Klenow fragment, and reacting were repeated nine times. These results confirm the improved specificity of the amplification reaction employing the thermostable enzyme herein.

In a later cloning experiment with GM2064 and the contaminated primers, 43 out of 510 colorless plaques (8%) had the (+)-strand insert. This suggests that approximately one-half of the 119 clones from Molt 4 contain the contaminant sequence.

Ten of the (+)-strand clones from Molt 4 were sequenced. Five were normal wild-type sequence and five had a single C to T mutation in the third position of the second codon of the gene (CAC to CAT). Four of the contaminant clones from GM2064 were sequenced and all four were normal.

Restriction site-modified primers may also be used to amplify and clone and partially sequence the human N-ras oncogene and to clone segments of the HLA DQ-α, DQ-β and DR-β genes using the above technique.

Again, if the concentrations of $MgCl_2$ and nucleotides are reduced to 2 mM and 150–200 μM, respectively, and the minimum cycling temperature is increased from 37° C. to 45–58° C., the specificity and efficiency of the amplification reaction can be increased.

EXAMPLE IV cDNA was made from 1 μg of rabbit reticulocyte mRNA (Bethesda Research Laboratories) in a 100 μl reaction volume containing 150 mM KCl, 50 mM Tris,HCl (pH 8.3), 10 mM $MgCl_2$, 5 mM DTT, 0.5 mM dATP, 0.5 mM dCTP, 0.5 mM TTP, 0.5 mM dGTP, 0.2 μg oligo(dT)12–18 (Pharmacia), 40 units RNasin (Promega Biotec), and 5 units AMV reverse transcriptase (BRL) and incubated for 30 minutes at 42° C. The reaction was stopped by heating for 10 minutes at 95° C. Two μg RNase A was added to the sample (2 μl of a 2 mg/ml solution in water) and incubated for 10 minutes at 37° C.

Three amplification reactions were done with the Klenow fragment using different pairs of primers. The primer pair PC03/PC04 define a 110-bp product. The primer pair RS45/oligo(dT)25–30 define an about 370-bp product, and the primer pair PC03/oligo(dT)25–30 an about 600-bp product. PC03, PC04, and RS45 are complementary to the human β-globin gene and each has two mismatches with the rabbit gene. PC03 and PC04 are described in Example I. RS45 has the sequence: 5'-CAAGAAGGTGCTAGGTGCC-3'.

The amplification reactions were performed with 1/20th (5 μl of the cDNA described above in a 100 μl reaction volume containing 50 mM NaCl, 10 mM Tris.HCl (pH 7.6), 10 mM $MgCl_2$, 200 μg/ml gelatin, 10% DMSO, 1 μM PC03 or RS45, 1 μM PC04 or oligo(dT)25–30, 1.5 mM dATP, 1.5 mM dCTP, 1.5 mM TTP and 1.5 mM dGTP. The samples were heated for five minutes at 98° C., then cooled to room temperature and overlayed with 100 μl mineral oil.

The samples were subjected to 10 cycles of automated amplification using the machine described in Example I and using the following program:
 1) heating from 37° C. to 98° C. in a heating block over 2.5 minutes (denature);
 2) cooling from 98° C. to 37° C. over 3.0 minutes (anneal);
 3) adding 1 unit Klenow fragment; and
 4) maintaining at 37° C. for 20 minutes (extend).
The final volume of each sample was about 140 μl.

One-twentieth (7 μl) of each sample was analyzed by electrophoresis on a 2% agarose gel. After staining with ethidium bromide, discrete bands were seen in the PC03/PC04 and RS45/oligo(dT) samples. The sizes of the bands were consistent with the expected lengths: 110-bp for the former, about 370-bp for the latter. No evidence of amplification of an about 600-bp fragment with the PC03/oligo(dT) primer pair was observed.

The contents of the gel were Southern blotted onto a Genatran nylon membrane and hybridized with a nick-translated human β-globin probe, pBR328:betaA, described in Saiki et al., *Science*, supra, using standard techniques. The resulting autoradiogram extended the conclusions reached previously—the 110 and about 370-bp fragments were β-globin specific amplification products and no significant amplification of the about 600-bp band was detected.

Three additional samples were amplified with the Taq polymerase obtained as described above using the same primer pairs described previously. Five microliter portions of cDNA were amplified in 100 μl reaction volumes containing 50 mM KCl, 25 mM Tris.HCl (pH 8.0), 10 mM $MgCl_2$, 200 μg/ml gelatin, 10% DMSO, 1 μM PC03 or RS45, 1 μM PC04 or oligo-(dT)25–30, 1.5 mM dATP, 1.5 mM dCTP, 1.5 mM TTP and 1.5 mM dGTP. The samples were heated for five minutes at 98° C., then cooled to room temperature. One microliter of Taq polymerase (1/8 dilution of lot 2) was added to each and overlayed with about 100 μl mineral oil.

The samples were subjected to 9 cycles of amplification in the Peltier device described in the previous example using the following program:
 1) 1 min., 35 to 60° C. ramp;
 2) 12 min., 60 to 70° C. ramp (extend);.
 3) 1 min., 70–95° C. ramp (denature);
 4) 30 sec., 95° C. soak;
 5) 1 min., 95 to 35° C. ramp (anneal); and
 6) 30 sec., 35° C. soak.
After the last cycle, the samples were incubated an additional 10 minutes at 70° C. to complete the final (10th cycle) extension. The final volume of each was about 100 μl.

As before, 1/20th (10 μl) of each sample was analyzed on a 2% agarose gel. In this gel, amplification products were present in all three samples: 110-bp for PC03/PC04, about 370-bp for RS45/oligo(dT), and about 600-bp for PC03/oligo(dT). These results were confirmed by Southern transfer and hybridization with the pBR328:betaA probe.

The production of the 600-bp product with Taq polymerase but not with the Klenow fragment is significant, and suggests that Taq polymerase is capable of producing longer DNA than the Klenow fragment.

EXAMPLE V

The Taq polymerase purified as described in Example VI of U.S. Ser. No. 063,509, filed Jun. 17, 1987, which issued as U.S. Pat. No. 4,889,818 was diluted in a buffer described in that same copending U.S. application.

A reaction buffer was then prepared containing 50 mM KCl, 10 mM Tris-Cl, pH 8.3, 1.5 mM MgCl$_2$, 0.01% (w/v) gelatin, 200 µM each dNTP, 1 µM each of the primers that define a 500 base pair target sequence on a control template from bacteriophage λ, and 2.0–2.5 units Taq polymerase/ assay in a final volume of 100 µl. Template was added to the reaction buffer, the sample placed in a 0.5 ml polypropylene tube, and the sample topped with 100 µl of heavy white mineral oil to prevent evaporation. [One unit of enzyme activity is defined as the amount of enzyme that will incorporate 10 nmoles of dNTPs into acid-insoluble material in 30 minutes at 74° C. Enzyme activity was assayed using the conditions of 25 mM TAPS-Cl pH 9.3, 50 mM KCl, 2 mM MgCl$_2$, 1 mM β-mercaptoethanol, 200 µM each dATP, dGTP, and TTP, 100 µM dCTP (mix cold and [α-$^{32}$P]), 250 µg activated salmon sperm DNA, in final volume of 50 µl.]

At least a 10$^5$-fold amplification was achieved when the following cycling conditions were employed, using 1 ng of control template (bacteriophage λ DNA) where the target sequence represented approximately 1% of the starting mass of DNA.

First the template mixture was denatured for one minute, 30 seconds at 94° C. by placing the tube in a heat bath. Then the tube was placed in a heat bath at 37° C. for two minutes. Then the tube was placed in a heat bath at 72° C. for three minutes, and then in the heat bath at 94° C. for one minute. This cycle was repeated for a total of 25 cycles. At the end of the 25th cycle, the heat denaturation step at 94° C. was omitted and replaced by extending the 72° C. incubation step by an additional three minutes. Following termination of the assay, the samples were allowed to cool to room temperature and analyzed as described in previous examples.

The template may be optimally amplified with a different concentration of dNTPs and a different amount of Taq polymerase. Also, the size of the target sequence in the DNA sample will directly impact the minimum time required for proper extension (72° C. incubation step). An optimization of the temperature cycling profile should be performed for each individual template to be amplified, to obtain maximum efficiency.

EXAMPLE VI

Several 1 µg samples of human genomic DNA were subjected to 20–35 cycles of amplification as described in Example V, with equivalent units of either Klenow fragment or Taq polymerase, and analyzed by agarose gel electrophoresis and Southern blot. The primers used in these reactions, PC03 and PC04, direct the synthesis of a 110-bp segment of the human beta-globin gene. The Klenow polymerase amplifications exhibited the smear of DNA typically observed with this enzyme, the apparent cause of which is the non-specific annealing and extension of primers to unrelated genomic sequences under what were essentially non-stringent hybridization conditions (1× Klenow salts at 37° C.). Nevertheless, by Southern blot a specific 110-bp beta-globin target fragment was detected in all lanes. A substantially different electrophoretic pattern was seen in the amplifications done with Taq polymerase where the single major band is the 110-bp target sequence. This remarkable specificity was undoubtedly due to the temperature at which the primers were extended.

Although, like Klenow fragment amplifications, the annealing step was performed at 37° C., the temperature of Taq-catalyzed reactions had to be raised to about 70° C. before the enzyme exhibited significant activity. During this transition from 37 to 70° C., poorly matched primer-template hybrids (which formed at 37° C.) disassociated so that by the time the reaction reached an enzyme-activating temperature, only highly complementary substrate was available for extension. This specificity also results in a greater yield of target sequence than similar amplifications done with Klenow fragment because the non- specific extension products effectively compete for the polymerase thereby reducing the amount of 110-mer that can be made by the Klenow fragment.

EXAMPLE VII

Amplification was carried out of a sample containing 1 µg Molt 4 DNA, 50 mM KCl, 10 mM Tris pH 8.3, 10 mM MgCl$_2$, 0.01% gelatin, 1 µM of each of the following primers (to amplify a 150 bp region):

5'-CATGCCTCTTTGCACCATTC-3'     (RS79)

and

5'-TGGTAGCTGGATTGTAGCTG-3'     (RS80)

1.5 mM of each dNTP, and 5.0 units of Taq polymerase per 100 µl reaction volume. Three additional samples were prepared containing 2.5, 1.3, or 0.6 units of Taq polymerase. The amplification was carried out in the temperature cycling machine described above using the following cycle, for 30 cycles:

from 70 to 98° C. for 1 minute hold at 98° C. for 1 minute from 98° C. to 35, 45 or 55° C. for 1 minute hold at 35, 45 or 55° C. for 1 minute from 35, 45 or 55° C. to 70° C. for 1 minute hold at 70° C. for 30 seconds At 35° C. annealing temperature, the 2.5 units/100 µl Taq enzyme dilution gave the best-signal-to noise ratio by agarose gel electrophoresis over all other Taq polymerase concentrations. At 45° C., the 5 units/100 µl Taq enzyme gave the best signal-to-noise ratio over the other concentrations. At 55° C., the 5 units/100 µl Taq enzyme gave the best signal-to-noise ratio over the other concentrations and over the 45° C. annealing and improved yield. The Taq polymerase has more specificity and better yield at 55° C.

In a separate experiment the Molt 4 DNA was 10-fold serially diluted into the cell line GM2064 DNA, containing no β- or δ-globin sequences, available from the Human Genetic Mutant Cell Depository, Camden, N.J., at various concentrations representing varying copies per cell, and amplification was carried out on these samples as described in this example at annealing temperatures of 35° C. and 55° C. At 35° C., the best that can be seen by agarose gel electrophoresis is 1 copy in 50 cells. At 55° C., the best that can be seen is 1/5,000 cells (a 100-fold improvement over the lower temperature), illustrating the importance of increased annealing temperature for Taq polymerase specificity under these conditions.

In a third experiment, DNA from a cell line 368H containing HIV-positive DNA, available from B. Poiesz, State University of New York, Syracuse, N.Y., was similarly diluted into the DNA from the SC1 cell line (deposited with ATCC on Mar. 19, 1985; an EBV-transformed B cell line homozygous for the sickle cell allele and lacking any HIV sequences) at various concentrations representing varying copies per cell, and amplification was carried out as described in this Example at annealing temperatures of 35°

C. and 55° C., using the primers SK38 and SK39, which amplify a 115 bp region of the HIV sequence:

5'-ATAATCCACCTATCCCAGTAGGAGAAAT-3' (SK38)

and

5'-TTTGGTCCTTGTCTTATGTCCAGAATGC-3' (SK39)

The results by agarose gel electrophoresis showed that only the undiluted 368H sample could be detected with the annealing temperature at 35° C., whereas at least a $10^{-2}$ dilution can be detected with the annealing temperature at 55° C., giving a 100-fold improvement in detection.

In summary, the present invention is seen to provide a process for amplifying one or more specific nucleic acid sequences using a temperature-cycled chain reaction and a thermostable enzyme, in which reaction primer extension products are produced that can subsequently act as templates for further primer extension reactions. The process is especially useful in detecting nucleic acid sequences that are initially present in only very small amounts and in detecting nucleotide variations using sequence-specific oligonucleotides. Also, the amplification process herein can be used for molecular cloning.

The process herein results in increased yields of amplified product, greater specificity, and fewer steps necessary to carry out the amplification procedure, over what has been previously disclosed.

Other modifications of the above-described embodiments of the invention that are obvious to those of skill in the area of molecular biology and related disciplines are intended to be within the scope of the following claims.

What is claimed is:

1. A kit for the amplification of a nucleic acid, said kit comprising:

(a) first and second oligonucleotide primers, said oligonucleotide primers differing in sequence from each other;

(b) an oligonucleotide probe that differs in sequence from said first and second oligonucleotide primers; and (c) a DNA polymerase enzyme.

2. The kit according to claim 1 wherein said oligonucleotide probe is labeled with a detectable label moiety.

3. The kit according to claim 2 which further comprises four different nucleoside triphosphates.

4. The kit according to claim 1 which further comprises four different nucleoside triphosphates.

5. The kit according to claim 1 in which said two oligonucleotide primers each contain about 15 to 25 nucleotides.

6. The kit according to claim 1 in which at least one of said first and second oligonucleotide primers contains a restriction site.

7. The kit according to claim 1 in which said first and second oligonucleotide primers have the nucleic acid sequences ACACAACTGTGTTCACTAGC and CAACTTCATCCACGTTCACC.

* * * * *

Disclaimer 6,040,166—Henry A. Erlich, Oakland; Glenn Horn, Emeryville; Randall K. Saiki, Richmond; Kary B. Mullis, La Jolla; David H. Gelfand, Oakland, all of Calif. KITS FOR AMPLIFYING AND DETECTING NUCLEIC ACID SEQUENCES, INCLUDING A PROBE. Patent dated March 21, 2000. Disclaimer filed November 2, 2000, by the assignee, Roche Molecular Systems, Inc.

The term of this patent shall not extend beyond the expiration date of Pat. No. 5,176,995.
*(Official Gazette, March 6, 2001)*